United States Patent
Barbosa et al.

(10) Patent No.: US 10,307,308 B2
(45) Date of Patent: Jun. 4, 2019

(54) ABSORBENT ARTICLE DEMONSTRATING CONTROLLED DEFORMATION AND LONGITUDINAL FLUID DISTRIBUTION

(71) Applicant: JOHNSON & JOHNSON CONSUMER INC., Skillman, NJ (US)

(72) Inventors: Livea Fujita Barbosa, Sao Paulo (BR); Felipe Boni Rezende, Sao Paulo (BR); Leonard Rosenfeld, Yardley, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 659 days.

(21) Appl. No.: 14/645,902

(22) Filed: Mar. 12, 2015

(65) Prior Publication Data
US 2016/0089277 A1 Mar. 31, 2016

Related U.S. Application Data

(60) Provisional application No. 62/057,590, filed on Sep. 30, 2014.

(51) Int. Cl.
| | | |
|---|---|---|
| *A61F 13/15* | (2006.01) | |
| *A61F 13/511* | (2006.01) | |
| *A61F 13/472* | (2006.01) | |
| *A61F 13/475* | (2006.01) | |
| *A61F 13/533* | (2006.01) | |
| *A61F 13/536* | (2006.01) | |
| *A61F 13/51* | (2006.01) | |

(52) U.S. Cl.
CPC .... *A61F 13/51108* (2013.01); *A61F 13/4756* (2013.01); *A61F 13/47218* (2013.01); *A61F 13/51104* (2013.01); *A61F 13/533* (2013.01); *A61F 13/536* (2013.01); *A61F 2013/51078* (2013.01)

(58) Field of Classification Search
CPC ............ A61F 13/4704; A61F 13/47218; A61F 13/47227; A61F 13/4756; A61F 13/474; A61F 13/472; A61F 13/47; A61F 13/51108; A61F 13/49001; A61F 13/51394; A61F 13/51104; A61F 13/51078; A61F 13/533; A61F 13/536
See application file for complete search history.

(56) References Cited

U.S. PATENT DOCUMENTS

| | | | |
|---|---|---|---|
| 4,555,430 A | 11/1985 | Mays | |
| 4,589,876 A | 5/1986 | Van Tilburg | |
| 4,608,047 A | 8/1986 | Mattingly | |
| 4,687,478 A | 8/1987 | Van Tillburg | |
| 4,795,455 A | 1/1989 | Luceri, et al. | |

(Continued)

FOREIGN PATENT DOCUMENTS

| | | | |
|---|---|---|---|
| EP | 1493415 A3 | 5/2006 | |
| EP | 2292200 A4 | 12/2012 | |

(Continued)

OTHER PUBLICATIONS

European Search Report, Application No. EP 15187476.1 dated Feb. 29, 2016.

*Primary Examiner* — Bradley H Philips

(57) ABSTRACT

The present invention generally relates to absorbent articles and in particular to a absorbent articles demonstrating controlled deformation and enhanced fluid wicking in the longitudinal direction of the absorbent articles.

13 Claims, 17 Drawing Sheets

(56) References Cited

U.S. PATENT DOCUMENTS

| | | | |
|---|---|---|---|
| 4,900,320 | A | 2/1990 | McCoy |
| 4,911,701 | A | 3/1990 | Mavinkurve |
| 5,171,302 | A | 12/1992 | Buell |
| 5,197,959 | A | 3/1993 | Buell |
| 5,507,736 | A | 4/1996 | Clear, et al. |
| 5,558,656 | A | 9/1996 | Bergman |
| 5,591,150 | A | 1/1997 | Olsen, et al. |
| 5,607,414 | A | 3/1997 | Richards, et al. |
| 5,722,967 | A | 3/1998 | Coles |
| 5,810,800 | A | 9/1998 | Hunter, et al. |
| 5,916,670 | A | 6/1999 | Tan, et al. |
| 7,601,144 | B2 | 10/2009 | Drevik |
| 7,686,790 | B2 | 3/2010 | Rasmussen, et al. |
| 7,854,822 | B2 | 12/2010 | Chmielewski, et al. |
| 2004/0015145 | A1 | 1/2004 | Miura et al. |
| 2005/0148971 | A1 | 7/2005 | Kuroda et al. |
| 2007/0219520 | A1 | 9/2007 | Rosenfeld et al. |
| 2011/0144604 | A1 | 6/2011 | Noda et al. |
| 2011/0203355 | A1 | 8/2011 | Lindner et al. |
| 2012/0004633 | A1* | 1/2012 | Marcelo .............. A61F 13/4756 604/378 |

FOREIGN PATENT DOCUMENTS

| | | | |
|---|---|---|---|
| EP | 2281536 | A4 | 1/2013 |
| EP | 1818031 | B1 | 9/2013 |
| EP | 2246021 | B1 | 11/2014 |
| WO | 2004060253 | | 7/2004 |
| WO | 2012086265 | A1 | 6/2012 |
| WO | 201306530 | | 5/2013 |

* cited by examiner

ABSORBENT ARTICLE DEMONSTRATING CONTROLLED DEFORMATION AND LONGITUDINAL FLUID DISTRIBUTION

CROSS-REFERENCE TO RELATED APPLICATION

The present application claims the benefit of the earlier filing date of U.S. provisional patent application 62/057,590, filed Sep. 30, 2014, the entirety of which application is hereby incorporated by reference herein as if fully set forth herein.

FIELD OF INVENTION

The present invention generally relates to absorbent articles and in particular to absorbent articles demonstrating controlled deformation and enhanced fluid wicking or distribution in the longitudinal direction of the absorbent articles.

BACKGROUND OF THE INVENTION

In order for absorbent articles, such as sanitary napkins, to efficiently absorb a large amount of fluid during use it should effectively wick fluid throughout the absorbent structure of the absorbent article. Absent effective wicking properties, fluid such as menstrual fluid tends to pool in certain regions of the absorbent article. As a result, the full absorbent capacity of the absorbent article is not effectively utilized.

In addition to having effective wicking capabilities, such absorbent articles should also quickly or rapidly absorb fluid.

Under such circumstances (namely an article exhibiting effective wicking and rapid fluid absorption properties), the closer such an absorbent article is to the body, the faster it will absorb fluid exiting the body.

Accordingly, the inventors of the present invention have recognized a need for ide absorbent articles that comfortably and efficiently wick fluid in the longitudinal direction of the absorbent article while at the same time deforms into a hump for closer positioning to a user's body (i.e., the crotch or vaginal area).

Therefore, an aspect of the present invention is to provide an absorbent article which provides improved fluid wicking and at the same time, once deformed, exhibits a controlled deformation such that the absorbent article results in a hump deformation at a frequency of at least 75% of such deformations.

SUMMARY OF THE INVENTION

In certain embodiments, the present invention relates to an absorbent article having a transversely extending centerline and a longitudinally extending centerline and a body facing surface, the body facing surface comprising:

a central region having i) a first transverse side parallel to the transversely extending centerline and a second transverse side parallel to the transversely extending centerline and opposite the first transverse side in the direction of the longitudinally extending centerline; and ii) a first longitudinal side parallel to the longitudinally extending centerline and a second longitudinal side parallel to the longitudinally extending centerline and opposite the first longitudinal side in the direction of the transversely extending centerline, the central region comprising an embossing pattern comprising at least two longitudinally extending channels having respective ends thereof and interconnecting with each other, other than at their respective ends, to define at least one substantially non-embossed region;

a first longitudinal end region extending from the first transverse side of the central region directionally along the longitudinally extending centerline away from the central region, the first longitudinal end region comprising a first plurality of channels wherein at least one of the channels in the first plurality of channels extends directionally along the longitudinally extending centerline from the first transverse side across from about 50% to about 90% of the first longitudinal end region;

a second longitudinal end region extending from the second transverse side of the central region directionally along the longitudinally extending centerline and away from the of the central region, the second longitudinal end region comprising a second plurality of channels wherein at least one of the channels of the second plurality of channels extends directionally along the longitudinally extending centerline from the second transverse side across from about 50% to about 90% of the second longitudinal end region, the embossing pattern of the central region located longitudinally between and interconnected with the first and second plurality of channels at the respective ends of the at least two longitudinally extending channels of the embossing pattern of the central region;

a central longitudinal zone extending longitudinally across the first and second transverse end regions and the central region, the central longitudinal zone extending symmetrical about and directionally along the longitudinally extending centerline and comprising opposing longitudinally extending central longitudinal zone edges parallel to the longitudinally extending centerline defining a central longitudinal zone width W of from about 5 mm to about 20 mm, wherein the embossing pattern of the central region is located within and does not extend beyond the central longitudinal zone width W;

a first transverse end region extending from the first longitudinal side of the central region directionally along the transversely extending centerline and away from the central region, the first transverse end region comprising a least one first longitudinally extending outer channel spaced from about 5 mm to about 26 mm from the nearest central longitudinal zone edge; and a second transverse end region extending from the second longitudinal side of the central region directionally along the transversely extending centerline and away from the of the central region, the second transverse end region comprising a least one second longitudinally extending outer channel spaced from about 5 mm to about 26 mm from the nearest central longitudinal zone edge wherein the embossing pattern of the central region interconnects in fluid communication with the embossing patterns of the first and second longitudinal end regions.

In certain embodiments, the present invention relates to an absorbent article having a transversely extending centerline and a longitudinally extending centerline and a body facing surface, the body facing surface comprising:

a central region having i) a first transverse side parallel to the transversely extending centerline and a second transverse side parallel to the transversely extending centerline and opposite the first transverse side in the direction of the longitudinally extending centerline; and ii) a first longitudinal side parallel to the longitudinally extending centerline and a second longitudinal side parallel to the longitudinally extending centerline and opposite the first longitudinal side in the direction of the transversely extending centerline, the central region comprising an embossing pattern extending about and directionally along the longitudinally extending centerline;

a first longitudinal end region extending from the first transverse side of the central region directionally along the longitudinally extending centerline away from the central region, the first longitudinal end region comprising a first plurality of channels wherein at least one of the channels of the first plurality of channels extends along the longitudinally extending centerline directionally from the first transverse side across from about 50% to about 90% of the first longitudinal end region;

a second longitudinal end region extending from the second transverse side of the central region directionally along the longitudinally extending centerline and away from the of the central region, the second longitudinal end region comprising a second plurality of channels wherein at least one of the channels of the second plurality of channels extends along the longitudinally extending centerline directionally from the second transverse side across from about 50% to about 90% of the second longitudinal end region, the embossing pattern of the central region located longitudinally between and interconnected with the first and second plurality of channels;

a central longitudinal zone extending longitudinally across the first and second transverse end regions and the central region, the central longitudinal zone extending symmetrical about and directionally along the longitudinally extending centerline and comprising opposing longitudinally extending central longitudinal zone edges parallel to the longitudinally extending centerline defining a central longitudinal zone width W of from about 5 mm to about 20 mm, wherein the embossing pattern of the central region is located within and does not extend beyond the central longitudinal zone width W;

a first transverse end region extending from the first longitudinal side of the central region directionally along the transversely extending centerline and away from the central region, the first transverse end region comprising a least one first longitudinally extending outer channel spaced from about 5 mm to about 26 mm from the nearest central longitudinal zone edge; and a second transverse end region extending from the second longitudinal side of the central region directionally along the transversely extending centerline and away from the of the central region, the second transverse end region comprising a least one second longitudinally extending outer channel spaced from about 5 mm to about 26 mm from the nearest central longitudinal zone edge wherein the channels of the embossing pattern of the central region interconnects in fluid communication with the channels of the embossing patterns of the first and second longitudinal end regions; and wherein the embossing pattern of the central region, the embossing patterns of the first and second transverse end regions and the embossing patterns of the first and second longitudinal end regions cooperate to facilitate deformation of the article into a hump shaped deformation upon application of the article to a user's crotch region where the body facing surface is aligned to contact a user's body.

BRIEF DESCRIPTION OF THE DRAWINGS

Examples of embodiments of the present invention will now be described with reference to the drawings, in which.

DETAILED DESCRIPTION OF THE INVENTION

Figure 1:
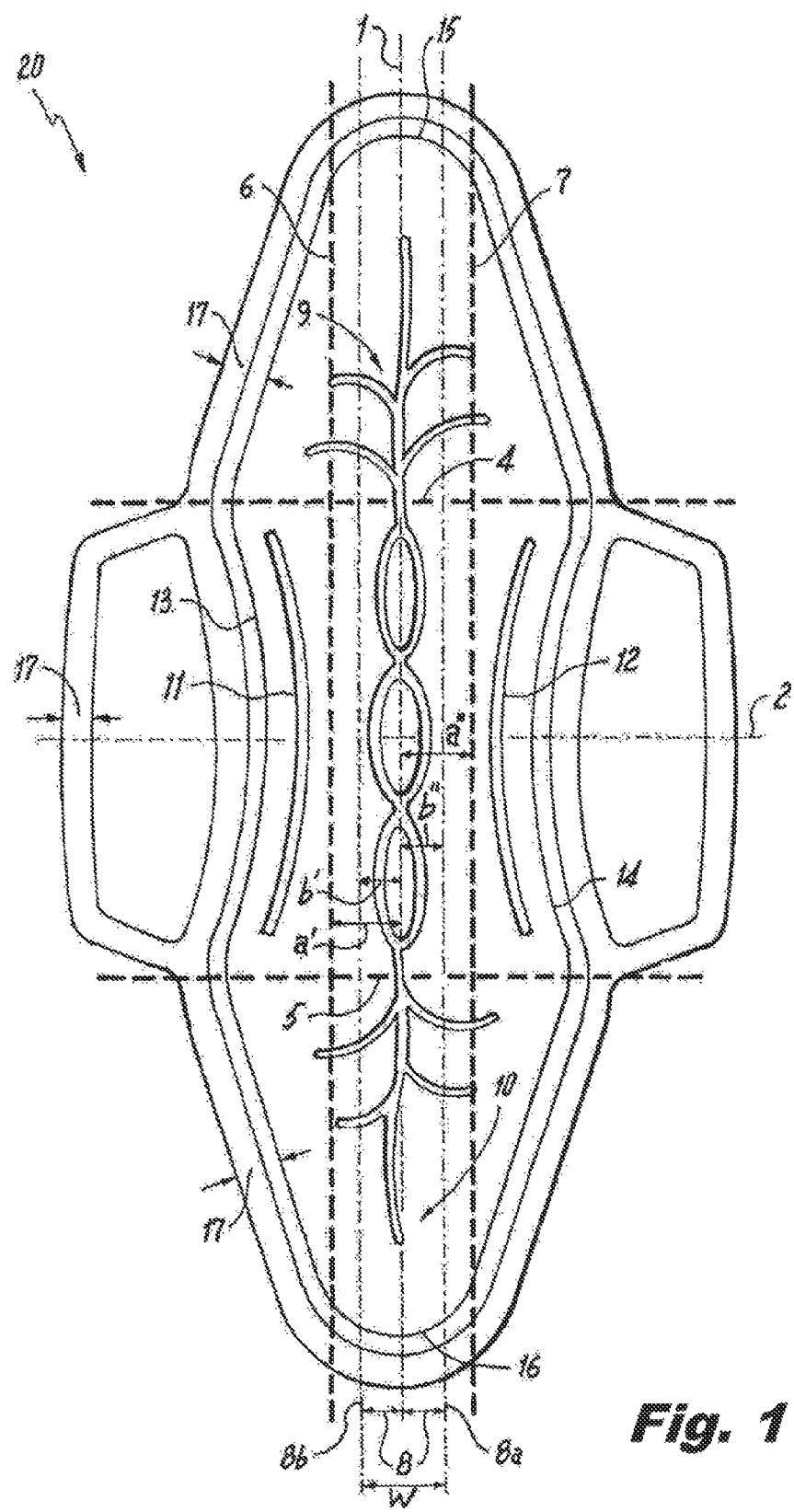
FIG. 1 is a top view of an embodiment of the embossing patterns of the articles of the present invention.

The articles of the present invention can comprise, consist of, or consist essentially of the essential elements and limitations of the invention described herein, as well any of the additional or optional features, components, or limitations described herein.

The term "comprising" (and its grammatical variations) as used herein is used in the inclusive sense of (and, interchangeably with the terms) "having" or "including" and not in the exclusive sense of "consisting only of." The terms "a" and "the" as used herein are understood to encompass the plural as well as the singular.

All documents incorporated herein by reference are only incorporated herein to the extent that they are not inconsistent with this specification.

All percentages, parts and ratios are based upon the total weight of the article of the present invention, unless otherwise specified.

In certain embodiments, the present invention as disclosed herein may be practiced in the absence of any compound, component or element (or group of compounds, components or elements) which is not specifically disclosed herein.

As used herein the term "controlled deformation" means deformation of an absorbent article which is controlled by the structure of the absorbent article, including any embossing features and/or patterns, in such a way that upon application of deformation forces (e.g., as generated when an absorbent article [e.g., sanitary napkin] is applied to and against the crotch of a user), the absorbent article predictably deforms into a hump so as to generally remain in contact with the crotch or vaginal area of the user.

As used herein, the term "hump" represents a configuration, upon visual inspection, of the absorbent article where, upon compression using the device 150 used in performing the Deformation/Distribution Test described below, the central longitudinal zone 8 (as defined below herein) has risen vertically (in the positive direction of vertical axis z) along the longitudinally extending centerline 1 relative to (i.e., so as to be above) the portions (301a, 302a) of longitudinally extending regions (301, 302) that are nearest to the central longitudinal zone 8 (as illustrated in FIGS. 10-14), where longitudinally extending region 301 extends transversely away from longitudinally extending zone edge 8a across the length of the article and longitudinally extending region 302 extends transversely away from longitudinally extending zone edge 8b, across the length of the article in a direction opposite the direction of longitudinally extending region 301.

As used herein, the term "cup" represents a configuration, upon visual inspection, of the absorbent article where, upon compression using the device 150 used in performing the Deformation/Distribution Test described below, the central longitudinal zone 8 (as defined below herein) has descended vertically (in the negative direction of vertical axis z) along the longitudinally extending centerline 1 relative to (i.e., so as to be below) the portions (301a, 302a) of longitudinally extending regions (301, 302) that are nearest to the central longitudinal zone 8 (as illustrated in FIGS. 15-19).

As used herein, the term "bunch" represents a configuration, upon visual inspection, of the absorbent article where, upon compression using the device 150 used in performing the Deformation/Distribution Test described below, neither a hump nor cup is formed.

As used herein, the term "visual inspection" or "visually inspected" means that a human viewer can visually discern the presence of the subject matter under such inspection with the unaided eye (excepting standard corrective lenses adapted to compensate for near-sightedness, farsightedness, or stigmatism, or other corrected vision) in lighting at least equal to the illumination of a standard 75 watt incandescent white light bulb at a distance of about 0.25 meter.

The Absorbent Article

One embodiment of an absorbent article according to the present invention is illustrated in FIG. 1. In certain embodiments, the absorbent article, as illustrated by article 20, has a length (measured as the longest length from the first transverse edge 15 to the second transverse edge 16) of from about 170 mm to about 400 mm and a width (measured as the longest length from the first longitudinal edge 13 to the second longitudinal edge 14) of from about 40 mm to about 80 mm. The outer most region 17 of the absorbent article 20 represents the area in which the cover and barrier layers extend beyond the border edges of the absorbent core and, hence, does not include absorbent core; the region 17 is not measured as part of (or otherwise taken into consideration when measuring) the length, width and/or surface area of the absorbent articles of the present invention.

As illustrated in FIG. 1, the absorbent article includes a longitudinally extending centerline 1, a transversely extending centerline 2, a first longitudinal edge 13, a second longitudinal edge 14, a first transverse edge 15, a second transverse edge 16, a first longitudinal end region 9, a second longitudinal end region 10, a central region 3 located between the first longitudinal end and second longitudinal end regions, 9 and 10 (the central region 3 contacting the first and second longitudinal end regions 9 and 10 at first and second transverse sides 4 and 5 of the central region 3, respectively) and a central longitudinal zone 8 which extends longitudinally from one end of the article, namely the first transverse edge 15, to the other end of the article, namely the second transverse edge 16 and has opposing longitudinally extending zone edges 8a, 8b defining a central longitudinal zone width W of from 5 (or about 5) mm to 20 (or about 20) mm, optionally from 10 (or about 10) mm to 18 (or about 18) mm and wherein the central longitudinal zone width W is symmetrical about the longitudinally extending centerline 1. Central longitudinal zone width W is the total of widths b' and b", where b' and b" extend oppositely and equidistant from the longitudinal centerline 1.

In some embodiments of the present invention (such as in FIG. 1), the transverse centerline 2 may be equidistant between the first transverse edge 15 and the second transverse edge 16. In other embodiments, the absorbent article may be asymmetric from front to back so that the end intended to be placed to the rear of the vaginal opening (i.e, nearer the backside of the user) may be longer than the end intended to be placed forward of the vaginal opening (i.e., nearer the front of the user). Examples of this type of product are Sempre Livre Noturno Toque Suave com Abas available from Johnson and Johnson Brasil and Always ultrathin overnight from Proctor and Gamble USA. In these products, the transverse centerline will intersect the center of the wings 200 or an area meant to be positioned directly over the vaginal opening.

In certain embodiments, the length of the first and second longitudinal end regions 9, 10 (as measured from the outer most longitudinally extending edge of first transverse edge 15 or second transverse edge 16, respectively) ranges from about 30 mm to about 70 mm (or about ⅓ the longest length between the first transverse edge 15 and second transverse edge 16). In certain embodiments, the width of the first and second longitudinal end regions 9, 10 (measured as the longest length from the first longitudinal edge 13 to the second longitudinal edge 14 within the respective lengths of first or second longitudinal regions 9, 10) ranges from about 30 mm to about 70 mm. In certain embodiments, the length of the central region (measured as the length between the first and second longitudinal end regions 9, 10) ranges from about 55 mm to about 200 mm (about ⅓ to about ½ the longest length between the first transverse edge 15 and second transverse edge 16). In certain embodiments, the width of the central region 3 is the total of widths a' and a" extending, oppositely from the longitudinal centerline 1, where widths a' and a" range, independently, from about 15 mm to about 35 mm. The width a' terminates at a first longitudinal side 6 of the central region 3 and width a" terminates at a second longitudinal side 7 of the central region 3 of the central region 3 as illustrated at FIG. 1.

The First and Second End Embossing Patterns

Figure 2:
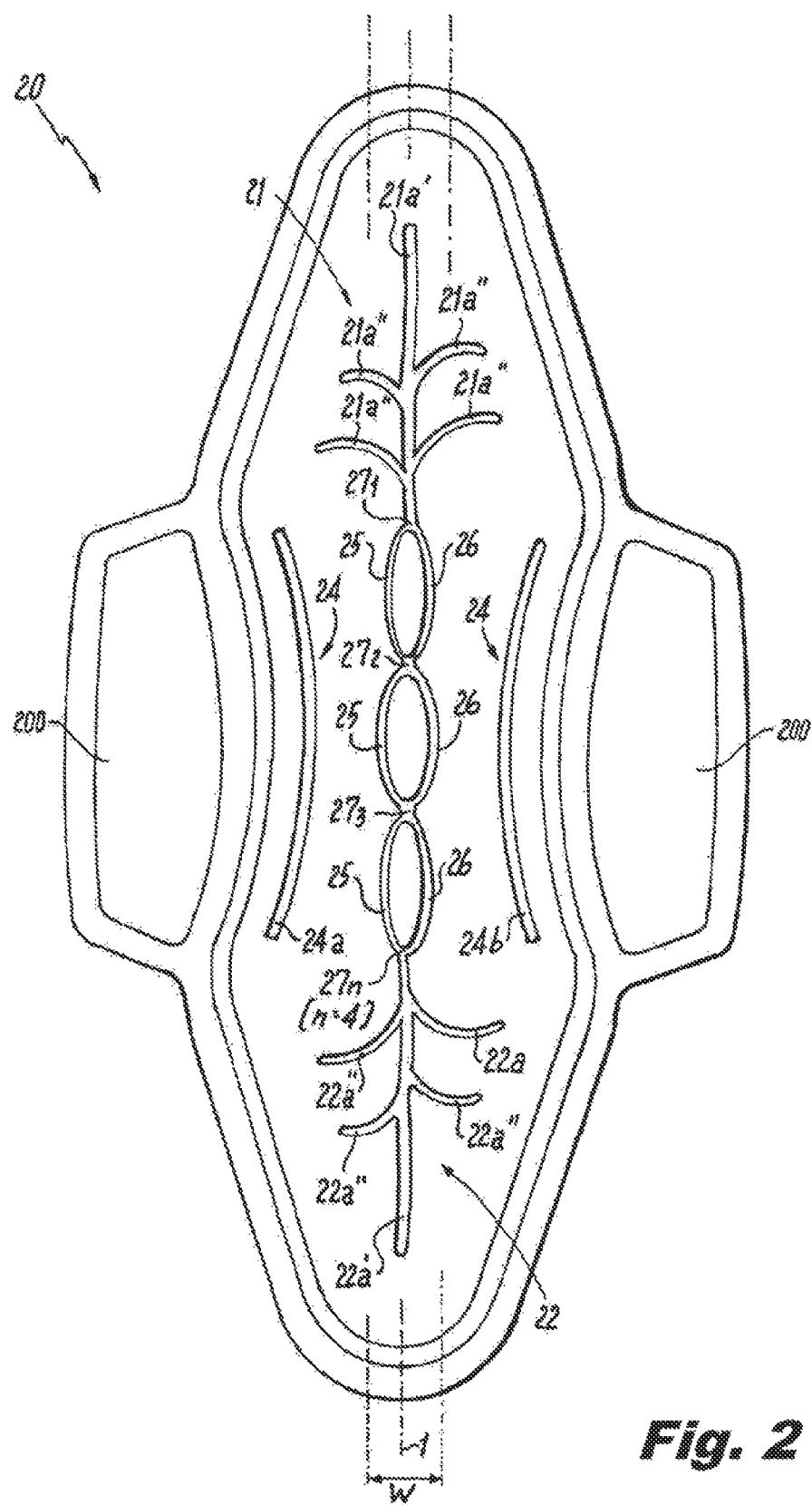
FIG. 2 is a top view of an embodiment of the embossing patterns of the articles of the present invention.

The absorbent article includes first and second end embossing patterns located opposite one another in the first and second longitudinal end regions, respectively, as illustrated in FIG. 2 in one embodiment by first and second end embossing patterns 21, 22 in the first and second longitudinal end regions 9, 10, respectively. Each of the first and second end embossing patterns 21, 22 of the first and second longitudinal end regions 9, 10, respectively, comprise, independently, a first and second plurality of channels 21a and 22a, respectively. In certain embodiments, the first and second plurality of channels 21a and 22a can be either branched as in FIGS. 1 and 4b (and portions of FIGS. 4a and 4d) or unbranched as in FIG. 4c (or portions of FIGS. 4a, and 4d). As the first end embossing pattern 21 is located within the first longitudinal end region 9 and second end embossing pattern 22 located in the second longitudinal end region 10, the first plurality of channels 21a of the first end embossing pattern 21 are spaced from the second plurality of channels 22a of the second end embossing pattern 22 in the longitudinal direction of longitudinally extending centerline 1. The first and second plurality of channels 21a, 22a can be similar in design or pattern or, optionally, different in design or pattern. In certain embodiments, the channels forming each of the first and second plurality of channels 21a, 22a are interconnected with each other either directly or through other channels including the channels of the central embossing pattern described herein in further detail below. The interconnection of channels is meant to promote distribution of absorbed fluid throughout the product.

The first and second plurality of channels 21a and 22a, each, comprise at least one longitudinally extending channel 21a' (first longitudinally extending channels) and 22a' (second longitudinally extending channels) in the first and second longitudinal end regions 9, 10, respectively, each longitudinally extending channel 21a' and 22a' of the first and second plurality of channels 21a and 22a extending, independently, directionally along or about (or, optionally overlapping or substantially overlapping) the longitudinally extending centerline 1 across from about 50% to about 90%, optionally from about 65% to about 90%, or optionally from about 70% to about 90% of the first and/or second longitudinal end regions 9, 10, respectively.

In certain embodiments, the channels of the first and second plurality of channels 21a and 22a, including the longitudinally extending channels 21a' and/or 22a' of the first and second longitudinal end regions 9, 10, optionally, comprise at least one (optionally, at least 2, optionally, at least 3, optionally, at least 4) branch(es) 21a" (first branch[es]) and/or 22a" (second branch[es]), respectively. In certain embodiments, the longitudinally extending channels 21a' and/or 22a' of the first and second longitudinal end regions 9, 10, each, comprise at least one (optionally, at least 2, optionally, at least 3, optionally, at least 4) branch(es) 21a" (first branch[es]) and/or 22a" (second branch[es]), respectively, extending, independently, from the longitudinally extending channels 21a' and/or 22a'. In certain embodiments, one or more of the first and/or second branch(es) 21a", 22a" extend from the longitudinally extending channels 21a' and/or 22a' such that another of the first and/or second branch(es) 21a", 22a" similarly extend oppositely from and symmetrically or substantially symmetrically (i.e., staggered or off set) with such first mentioned branch(es) with respect to the other side of longitudinally extending channels 21a' and/or 22a', respectively. In certain embodiments, the first and second plurality of channels 21a and 22a, respectively, comprise, independently, at least 2 (optionally, at least 3, optionally, at least 4) channels 21a and 22a, respectively.

The Central Embossing Pattern

The absorbent article of the present invention further includes a central embossing pattern as illustrated in one embodiment by the central embossing pattern 23. In certain embodiments, the central embossing pattern 23 of the central region 3 is located longitudinally between and interconnecting with the first and second plurality of channels 21a and 22a in the first and second longitudinal end regions 9, 10. The central embossing pattern 23 is located in the central region 3 of the absorbent article 20 wherein the central embossing pattern 23 is further located within the central longitudinal zone 8 and does not extend beyond the central longitudinal zone width W. In certain embodiments, the central embossing pattern 23 is an embossing pattern or design extending from the first transverse side 4 of the central region 3 to the second transverse side 5 of the central region 3 and about (optionally, symmetrically about) and directionally substantially along the longitudinally extending centerline 1. In certain other embodiments, the central embossing pattern comprises at least two (optionally from 2 to 12 optionally from 2 to 8) longitudinally extending channels, each having respective ends thereof, as illustrated by longitudinally extending channels 25, 26. In certain embodiments, the longitudinally extending channels 25, 26 are not connected, except at their respective ends. In certain embodiments, the longitudinally extending channels 25, 26 are interconnected at points other than at their respective ends. In certain other embodiments, the longitudinally extending channels 25, 26 are interconnected in the direction of (and, optionally, along or substantially along) the longitudinally extending centerline at nodes $27_1$ through $27_n$, where n is 1 (optionally 2 or greater, optionally from 2 to 100, optionally from 3 to 20) as illustrated in FIGS. 2 and 4b so as to form repeating, consistently or variably (including ascending and/or descending) sized, interconnected and longitudinally running shapes including, but not limited to, spherical shapes such as circles or ovals as shown in FIGS. 2 and 4c, box-shaped (i.e., resembling a box in rectangularity) shapes as shown in FIGS. 4b and 4d or irregular shapes such as shown in FIG. 4a. An example of ascending sized shapes can be seen in FIG. 4e. In certain embodiments, the longitudinally extending channels 25, 26 define at least one (optionally, at least two, optionally at least three, optionally 2 to 30, optionally 3 to 6) substantially non-embossed (or non-compressed) area(s) 28, the non-embossed area(s) 28 (see FIG. 3) is located within central longitudinal zone 8 and does not extend beyond the central longitudinal zone width W. In certain embodiments, the longitudinally extending channels 25 and 26 are arranged symmetrically and equidistant with respect to the longitudinally extending centerline 1. The term "substantially non-embossed" as used herein with respect to the area defined by the longitudinally extending channels means greater than from about 55% to about 100%, optionally from about 75% to about 100% of the area is non-embossed (or non-compressed).

Figure 3:
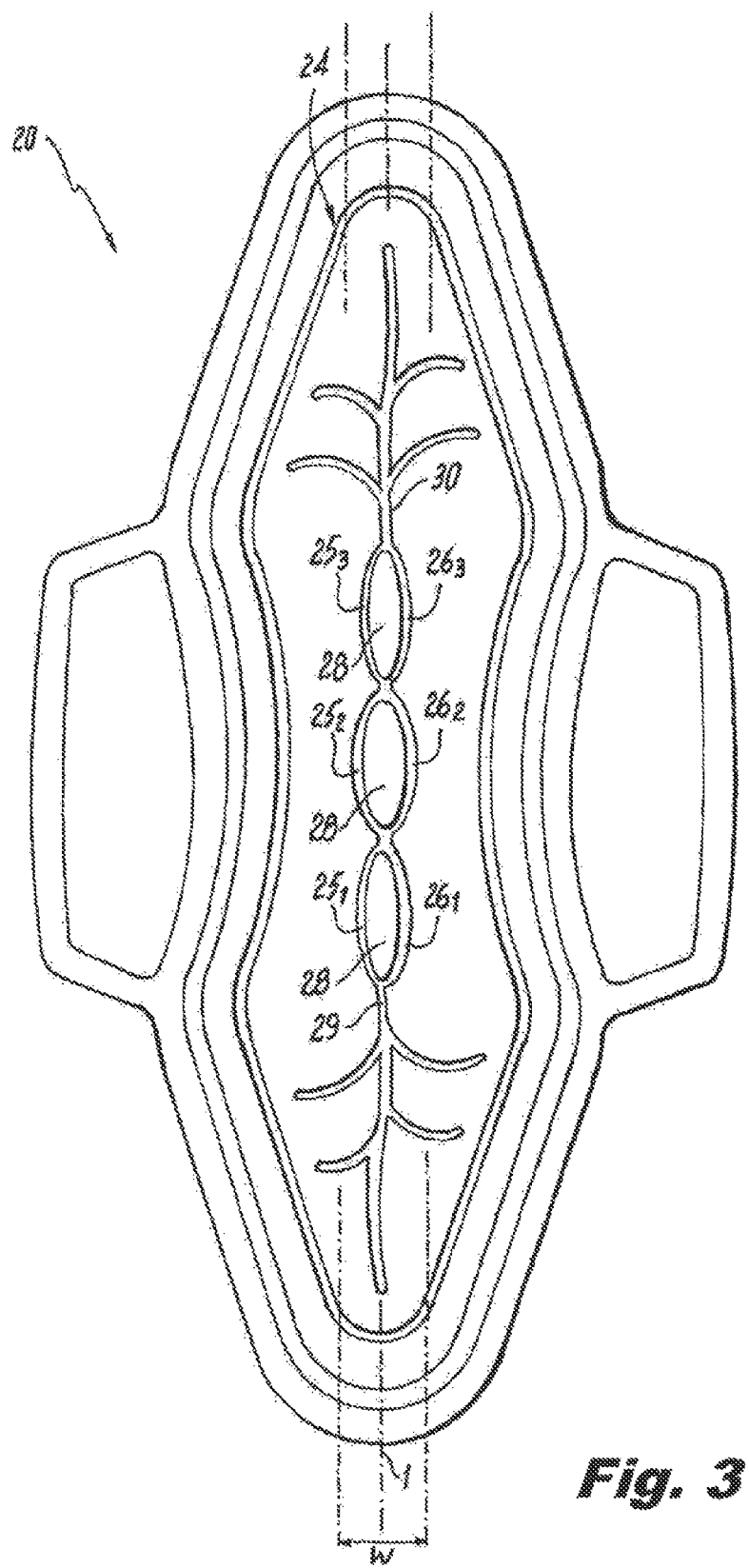
FIG. 3 is a top view of an embodiment of the embossing patterns of the articles of the present invention.
Figure 4A:
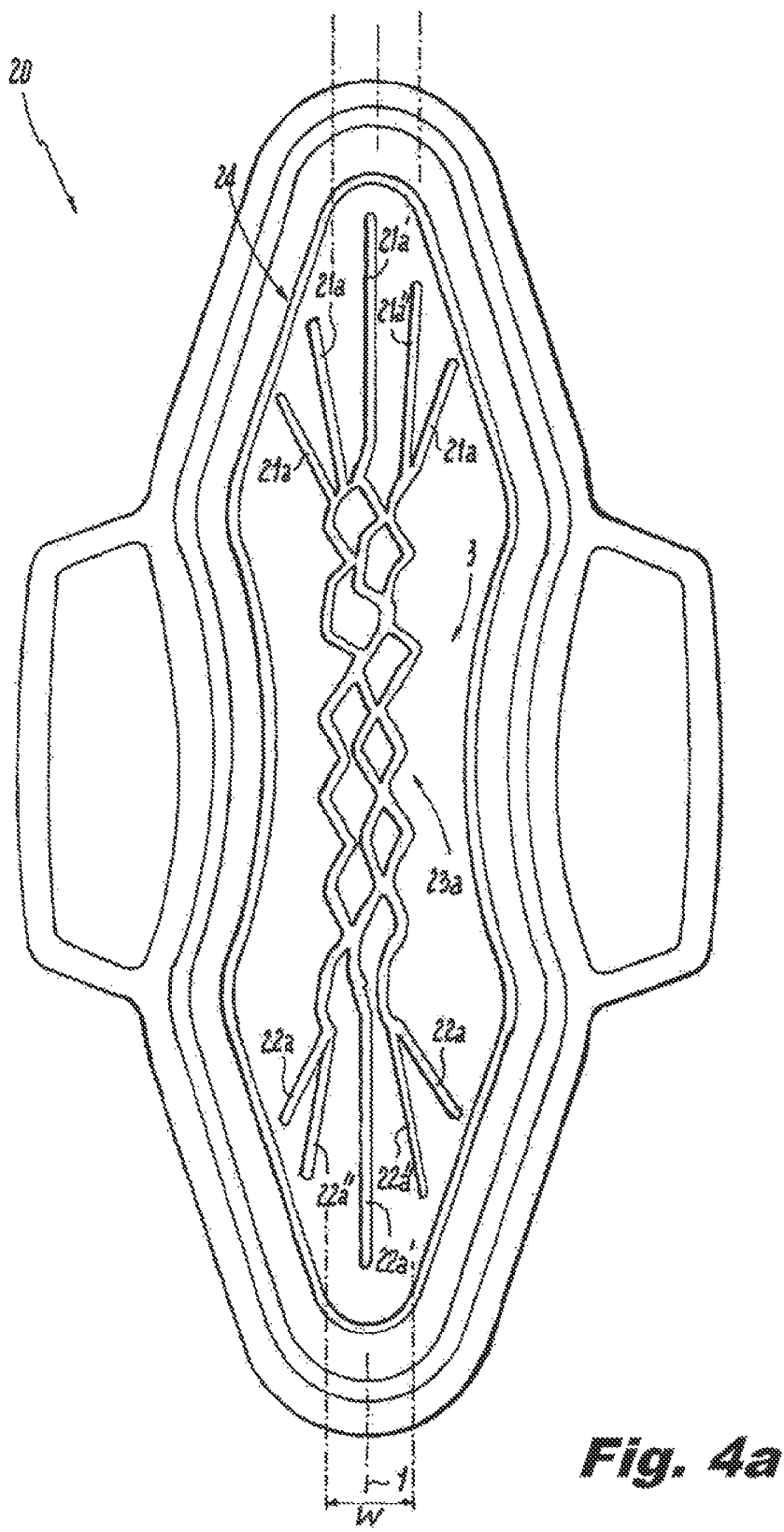
FIGS. 4*a* to 4*e* are top views of various embodiments of the embossing patterns of the central and longitudinal end regions of the articles of the present invention.
Figure 4B:
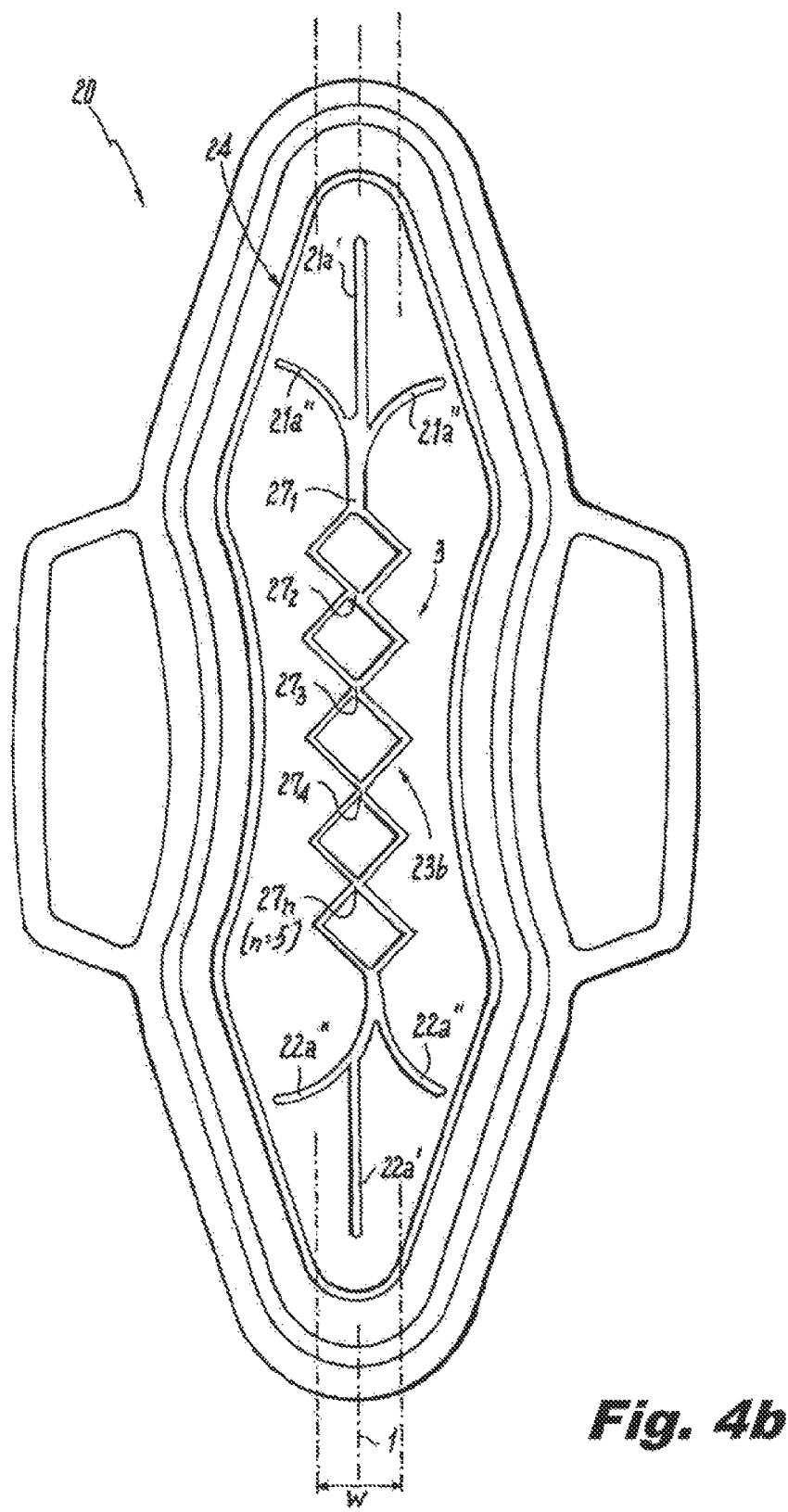
Figure 4C:
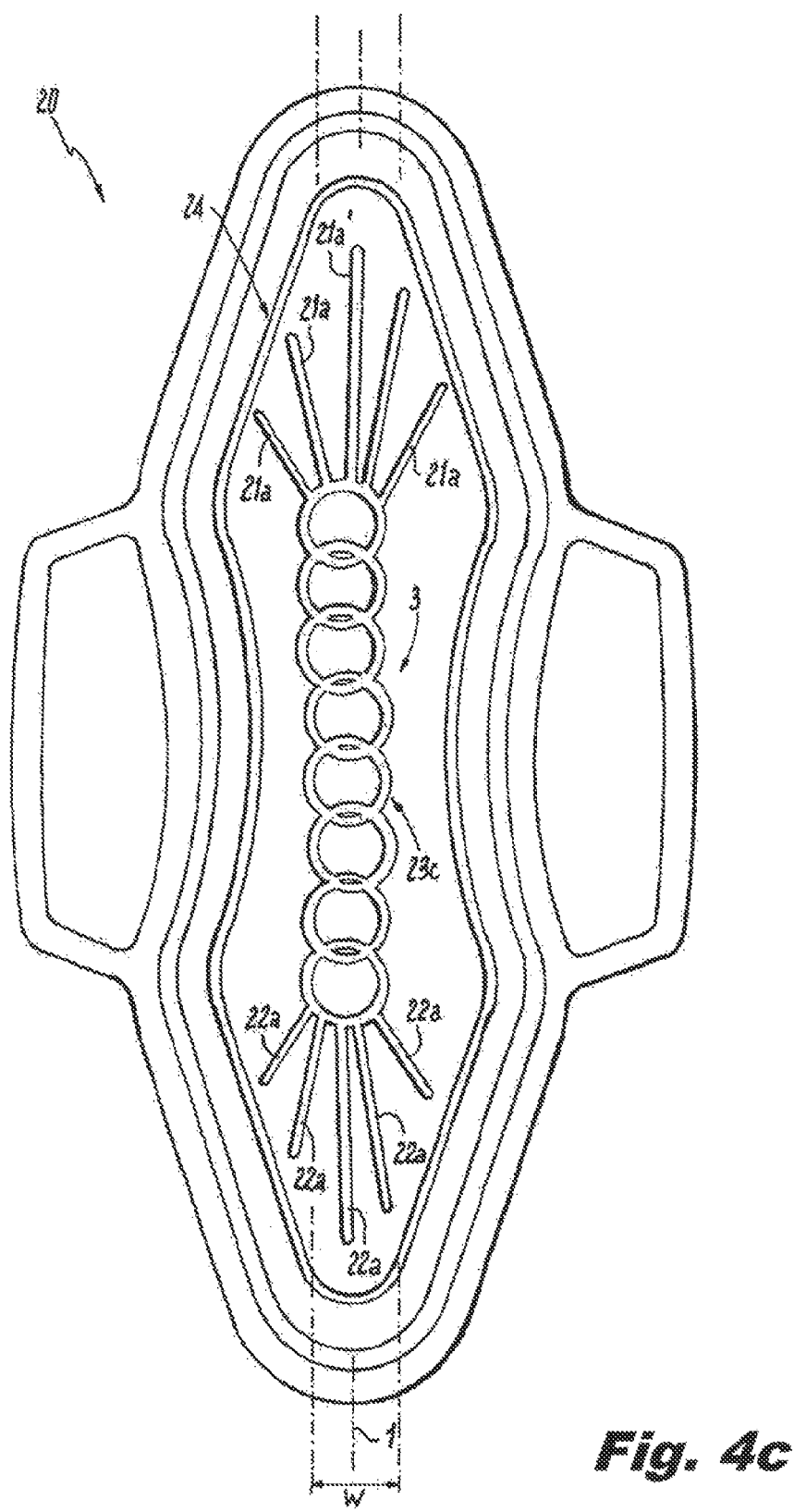
Figure 4D:
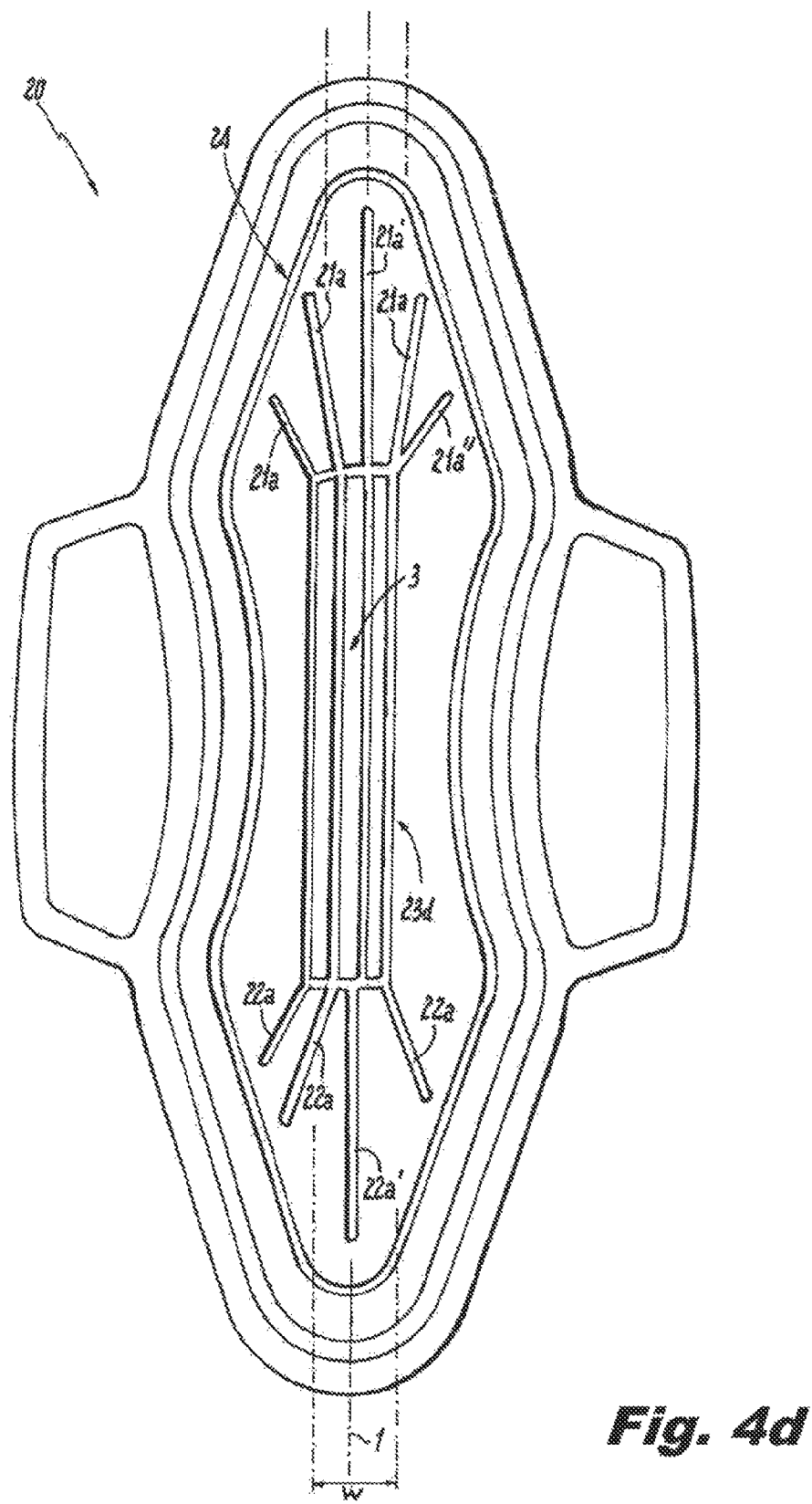
Figure 4E:
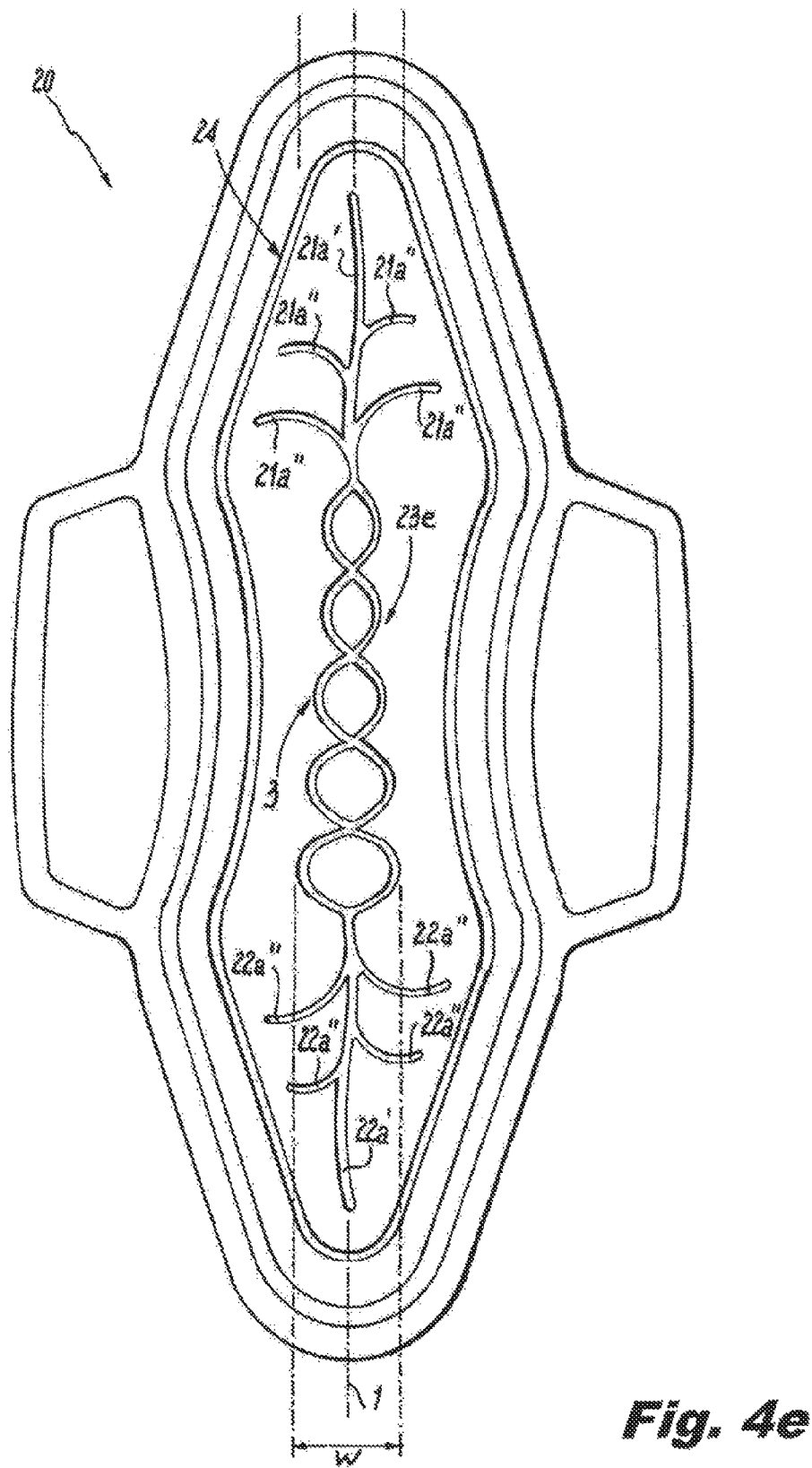

In certain embodiments, the longitudinally extending channels comprise longitudinally extending channel segments as illustrated by longitudinally extending channel segments $25_1$, $25_2$ and $25_3$ (optionally up to $25_n$, where n=30) and corresponding longitudinally extending channel segments $26_1$, $26_2$ and $26_3$ (optionally up to $26_n$, where n=30) as shown in FIG. 3. In certain embodiments, longitudinally extending channel segments $25_1$, $25_2$ and $25_3$ are positioned opposite corresponding longitudinally extending channel segments $26_1$, $26_2$ and $26_3$, respectively. Longitudinally extending channel segments $25_1$, $25_2$ and $25_3$ intersect corresponding longitudinally extending channel segments $26_1$, $26_2$ and $26_3$ at nodes $27_1$ through $27_n$ (optionally 2 or greater, optionally from 2 to 100, optionally from 3 to 20). In certain embodiments, the longitudinally extending channel segments $25_1$, $25_2$ and $25_3$ and corresponding longitudinally extending channel segments $26_1$, $26_2$ and $26_3$ are arranged, respectively, symmetrically and equidistant with respect to the longitudinally extending centerline 1. In further embodiments, longitudinally extending channel segments $25_1$, $25_2$ and $25_3$ and corresponding longitudinally extending channel segments $26_1$, $26_2$ and $26_3$ are concave with respect to the longitudinal extending center line 1. In certain embodiments, each one of the longitudinally extending channel segments, $25_1$, $25_2$ and $25_3$ and corresponding longitudinally extending channel segments $26_1$, $26_2$ and $26_3$ has a length in the range of about 3 cm to about 15 cm, optionally from about 4.5 cm to about 10 cm, when measured along a path of the longitudinally extending channel segments between nodes 27. In certain embodiments, each of longitudinally extending channel segments $25_1$, $25_2$ and $25_3$ and $26_1$, $26_2$ and $26_3$ has a width in the range of from about 1 mm to about 20 mm, optionally from about 2 mm to about 10 mm. In certain embodiments, each of the longitudinally extending channel segments $25_1$, $25_2$ and $25_3$ and $26_1$, $26_2$ and $26_3$ has a thickness in the range of from about 1 mm to about 10 mm, optionally between about 2 mm and about 5 mm, when measured from a top surface of the absorbent article 20 at the longitudinally extending channel segment. In certain embodiments, the length of the central embossing pattern ranges from 55 mm to 200 mm (or from about 33% to about 50% of the longest length from the first transverse edge 15 to the second transverse edge 16).

In other embodiments, the central embossing pattern 23 can take the form of the central embossing patterns 23a, 23b, 23c, 23d and 23e as illustrated, respectively, at FIGS. 4a to 4e.

In certain embodiments, the central embossing pattern 23 interconnects in fluid communication with the first and second end embossing patterns 21, 22, respectively (e.g., at the first transverse side 4 and the second transverse side 5, respectively or, alternatively, at the intersection 29 of first transverse side 4 and the longitudinally extending centerline 1 and intersection 30 of second transverse side 5 and the longitudinally extending centerline 1, respectively). In specific embodiments, the respective ends of the longitudinally extending channels interconnect in fluid communication at the first transverse side 4 and the second transverse side 5 (or at intersections 29, 30) with at least one (optionally 2 to 10, optionally 3 to 8, optionally 4-6) of the plurality of channels 21a and/or 22a, respectively, with at least one (optionally 2 to 10, optionally 3 to 8, optionally 4-6) of the first and second longitudinally extending channels 21a' and/or 22a' (i.e., along the longitudinally extending centerline 1), respectively, or (directly or indirectly) with at least one (optionally 2 to 10, optionally 3 to 8, optionally 4-6) of the first and second branches 21a'' and/or 22a'' of the first and second end embossing patterns 21, 22, respectively. The fluid communicating interconnection of channels 25 and 26, at the first transverse sides 4, 5 (or at intersections 29, 30), with the first and second end embossing patterns 21, 22 in both the first and second longitudinal end regions 9, 10, respectively, enables the absorbent article 20 to effectively and simultaneously wick fluid from the central region 3 of the absorbent article 20 to both the first and second longitudinal rend regions 9 and 10, respectively. In this manner, the full absorbent capacity of the absorbent article 20 is utilized.

In certain embodiments, the "channels" of the first and second end embossing patterns 21, 22, including the first and second plurality of channels 21a, 22a, the first and second longitudinally extending channels 21a', 22a' of the first and second plurality of channels 21a, 22a, and the first and second branches 21a'', 22a'' can, independently, be in the form of a straight channels or channels which are arcuate in shape (or in a combination of such shapes) and have a length in the range of about 2 cm to about 10 cm, optionally from about 5.0 cm to about 8.0 cm, when measured from the end of the such "channel" to the nearest of: i) the longitudinally extending channel 21a' or 22a' or ii) the initial node $27_1$ or ending node $27_n$, respectively, along the path of such channel. In certain embodiments, such "channels" have a width in the range of from about 1 mm to about 10 mm, optionally from about 2 mm to about 4.0 mm. In certain embodiments, the "channels" have a thickness of about 0.5 mm to about 2.5 mm, optionally about 1 mm to about 2 mm, when measured from a top surface of the absorbent article 20 at such channel. In certain embodiments, the first and second longitudinal extending channels 21a', 22a' of the first and second end embossing patterns 21, 22 do not extend outside the central longitudinal zone 8. In certain embodiments, the first and second branches 21a'', 22a'' extend outside the central longitudinal zone 8.

The "channels" and "branches" of the first and second end embossing patterns 21, 22 function to transport fluid towards the longitudinal end regions 3, 4 of the absorbent article 20 to thereby utilize the full absorbent capacity of the article along its length.

The Outer Embossing Pattern

The absorbent article of the present invention further includes an outer embossing pattern as illustrated in one embodiment by outer embossing pattern 24. In certain embodiments, the outer embossing pattern 24 comprises one or more (optionally, two or more) first and one or more (optionally, two or more) second longitudinally extending outer channels 24a, 24b, respectively, which one or more first and one or more second longitudinally extending outer channels 24a, 24b are independently shaped and oppositely positioned with respect to one another and at least partially separated by the central longitudinal zone 8. Each longitudinally extending outer channel 24a or 24b extends longitudinally at least partially across each of central longitudinal zone edges 8a and 8b and is spaced from 5 (or about 5) mm to 26 (or about 26) mm, optionally 10 (or about 10) mm to 20 (or about 20) mm, from the nearest central longitudinal zone edge 8a or 8b. In certain embodiments, the first and second longitudinally extending outer channels 24a, 24b can be the same or different in shape (or configuration). In certain embodiments, the one or more first longitudinally extending outer channels 24a are parallel to each other and, optionally, the one or more second longitudinally extending outer channels 24b are parallel to each other.

In one embodiment of the present invention, the longitudinally extending outer channels 24a, 24b are substantially equal in length to the length of the central region 3 shown in FIGS. 1 and 2. Alternatively, the respective ends of each of longitudinally extending outer channels 24a, 24b are extended so as to unite the respective ends of the other longitudinally extending outer channels (in fluid communication) such that the outer embossing pattern 24 surrounds or substantially surrounds the central embossing pattern and the first and second end embossing patterns as shown in FIGS. 3, 4a to 4d and 5. In certain embodiments, the longitudinally extending outer channels 24a, 24b are deep stitched or comprise a "dotted" pattern. In certain embodiments, the longitudinally extending outer channels 24a, 24b have a width of from about 1 mm to about 10 mm and a thickness of from about 0.5 mm to about 2.5 mm, when measured from a top surface of the absorbent article 20 at longitudinally extending outer channel 24a, 24b.

Without being limited by theory, it is believed that incorporating into the absorbent article of present invention the central embossing pattern, the first and second end embossing patterns and the outer embossing patterns, these embossing patterns cooperate so as to result in the absorbent article 20 having improved frequency of hump deformation. During use, the absorbent article will deform into the shape of a hump at a frequency of from about 75%, optionally about 90%, or optionally about 95%, to about 98%, optionally about 99%, or optionally about 100%, of such use related deformations (or simulated deformation, when measured by the Deformation/Distribution Test described below), resulting in the article conforming to and being in close contact with the user's body FIG. 12. These result in a more comfortable and efficient product.

In one embodiment of the invention, the central embossing pattern comprises two longitudinally extending channels 25 and 26, each extending the length of the central embossing pattern so as to only interconnect at the first transverse sides 4, 5 (or at intersections 29, 30). In one embodiment of the invention, longitudinally extending channels 25 and 26 further interconnect at one or more nodes 27.

In another embodiment of the invention, there are 4 interconnected longitudinally extending channel segments, segments $25_1$ and $25_2$ and corresponding segments $26_1$ and $26_2$, and the combined length of the channels extends the length of the central embossing pattern. In one embodiment of the present invention, channels $25_1$ and $25_2$ and $26_1$ and $26_2$ are connected at nodes $27_{(1-n)}$.

Figure 5:
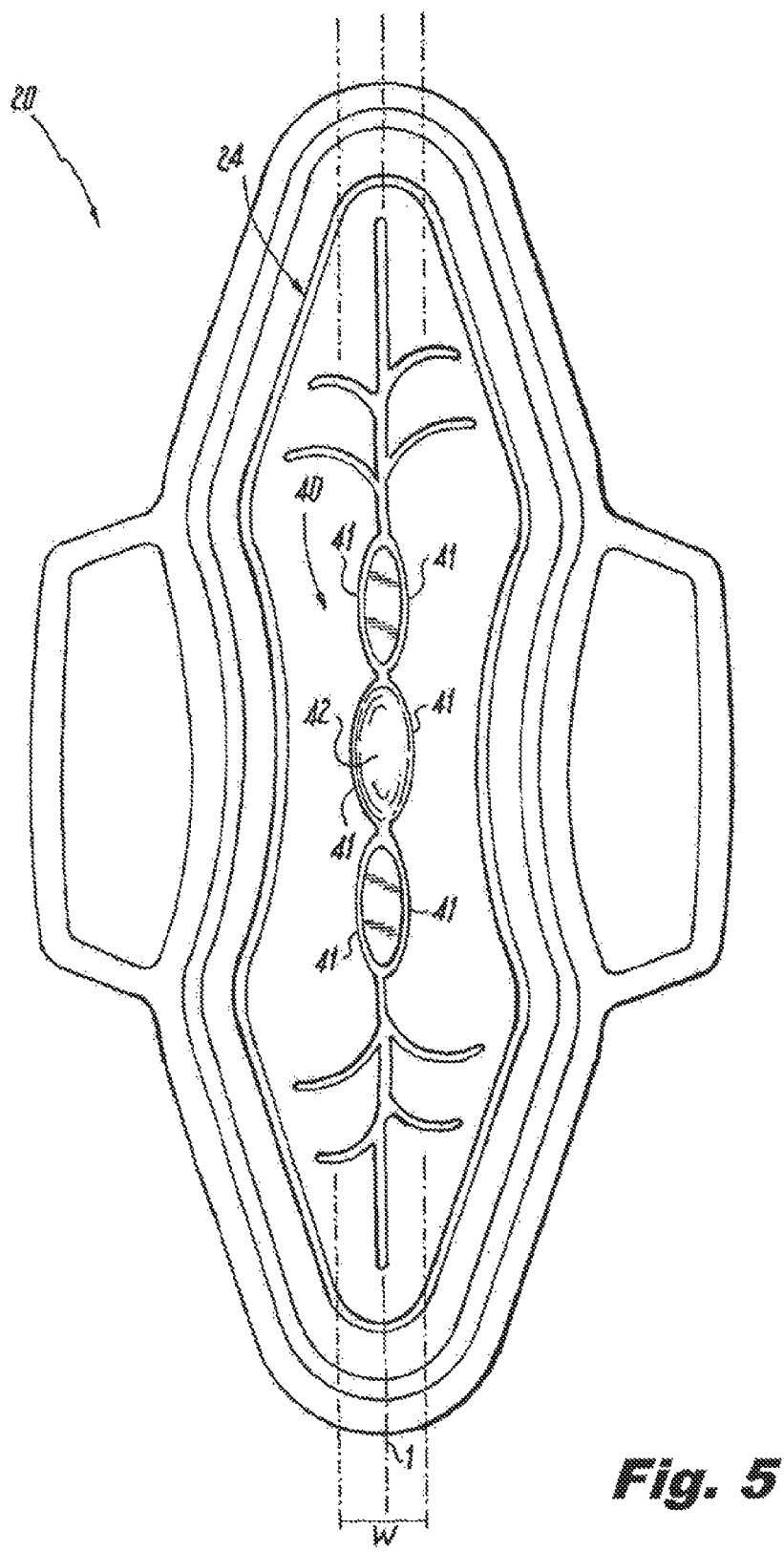
FIG. 5 is a top view of an embodiment of the embossing patterns of the articles of the present invention, illustrating embossed region 42.

In another embodiment of the present invention as illustrated at FIG. 5, the second (or central region) embossing pattern 40 having an outer embossed or compressed border 41 defining at least one (optionally, at least two, optionally at least three, optionally 2 to 30, optionally 3 to 6) substantially embossed (or compressed) area 42, the embossing pattern 40, including embossed area 42, located within central longitudinal zone and do not extend beyond central longitudinal zone width W. In certain embodiments, the area defined by outer embossed (or compressed) border 41 is similar in size and shape as the pattern of the central embossing pattern 23 of FIG. 1. The term "substantially embossed" as used herein with respect to the area defined by the outer embossed (or compressed) border 41 means greater than from about 55% to about 100%, optionally from about 75% to about 100% of the area is embossed.

The absorbent article may include a cover layer, a transfer layer, a core, a barrier layer and combinations thereof. The embossing patterns and channels are formed using conventional embossing techniques. The embossing roll used during manufacture should have surface features used to form the first, second and third embossing patterns. The embossing patterns result in areas of increased density. In one embodiment of the invention, the central area of the absorbent article includes from about 10% to about 50% areas of increased density.

The channels of the absorbent article may be provided with color, to thereby provide a color cue that is visible to a user from a top surface of the absorbent article. The color cue may be provided by printing colored regions to the cover layer. The colored regions optionally correspond in size, shape and location to the channels. The colored regions function to provide the user with a color cue to the presence and function of the channels. The colored regions could alternatively be printed on the absorbent layer provided that such colored regions can be viewed through the cover. Any means known to those of skill in the art may be utilized to provide the colored regions such as printing, utilizing colored fibers, or any other suitable means.

Embossing

Absorbent articles according to the invention have a thickness that may range from about 2 mm to about 20 mm in an uncompressed state. Where the absorbent article is compressed as a result of the embossing patterns described and utilized in the present invention, the thickness of the embossed area (or channels) may be measured with a Mitutoyo 547-516 thickness gauge or the like. For absorbent articles having an uncompressed thickness greater than 4 mm, the compressed thickness, unless otherwise specified herein, may range from about 0.5 mm (highly densified channel) to about 2.5 mm (lightly densified channel). For absorbent articles having an uncompressed thickness less than 4 mm, the compressed thickness may range from about 0.25 mm to about 2.0 mm.

The absorbent article is embossed (or compressed) and the thickness reduced in at least one layer but, optionally, in or through multiple layers or, optionally, in or through all the layers of the absorbent article. In general, thicker materials will undergo more thickness reduction. Accordingly, the layers which are actually embossed will, among other things, depend on the manufacturing process (e.g., which material is joined at the point where the embossing is applied).

The embossing can be achieved with standard techniques such as thermal bond, ultrasonic bond and/or pressure. An example of a suitable process is thermal bonding wherein the layers are passed through two steel rolls where one is engraved with the visual pattern and the other is flat. In certain embodiments, one or both of the rolls are warmed to temperature suitable to at least partially melt one or more layer (typical range from 90 to 170° C.).

The embossing roll may be engraved using conventional techniques such machine tooling for most embossing patterns, but it may be desirable to use acid etching or laser engraving to provide a finer engraving, and thus a finer embossed pattern. It may be desirable that the embossed pattern comprises relatively thin embossing features, much thinner than the embossed channels previously disclosed in the art, such as in U.S. Pat. Pub. No. 20040015145A1 to Miura et al., which publication is herein incorporated by reference. Thin embossing features may provide a generally feminine and delicate look to the article. The embossing tool should therefore capable of high definition embossing, in particular with a resolution (minimum thickness of the embossed lines) of less than about 0.75 mm, in particular but not limited to between about 0.35 mm and about 0.60 mm. Embossing of this type is often in the form of a plurality of lines where the product is embossed along the entire length of the lines. A second type of embossing that may be used is deep stitch embossing where a series of spots are embossed along a linear pattern. This type of embossing gives a can give a stitched appearance similar to sewn garments and fabrics. An example of this type of embossing is used in Whisper Choice napkins marketed by Proctor and Gamble Healthcare ltd, India.

Without being limited by theory, the embossing (or embossing patterns) of the absorbent articles of the present invention cooperate to produce the controlled deformation of the disclosed article. Such controlled deformation is achieved i) without the use of tensioned elastic materials as described in U.S. Pat. No. 4,911,701 to Mavinkurve, the specific disclosure of which materials is found in FIGS. 1-6 and at col. 3, line 10 to col. 4, line 3 and is herein incorporated by reference; in addition to the foregoing, the remainder of U.S. Pat. No. 4,911,701 is also herein incorporated by reference; the flexure-resistant deformation element described in U.S. Pat. No. 5,171,302 to Buell, the specific disclosure of which materials is found in FIGS. 1-27 and at col. 5, line 55 to col. 10, line 51 and is herein incorporated by reference; in addition to the foregoing, the remainder of U.S. Pat. No. 5,171,302 is also herein incorporated by reference or iii) such other non-embossing deformation causing materials as described in U.S. Pat. No. 7,601,144 to Drevik, the specific disclosure of which materials is found at col. 2, line 61 to col. 3, line 67 and which disclosure is herein incorporated by reference. Accordingly, in certain embodiments, the absorbent article of the present invention is free of non-embossing deformation causing materials or elements which are not embossing or embossing patterns.

Cover Layer

The cover layer may be a relatively low density, bulky, high-loft non-woven web material. The cover layer may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Optionally, the cover layer has a basis weight in the range of about 10 gsm to about 75 gsm.

Bi-component fibers may be made up of a polyester layer and a polyethylene sheath. The use of appropriate bi-component materials results in a fusible non-woven fabric. Examples of such fusible fabrics are described in U.S. Pat. No. 4,555,430 to Mays, which patent is herein incorporated by reference. Using a fusible fabric increases the ease with which the cover layer may be mounted to the absorbent layer and/or to the barrier layer.

The cover layer optionally has a relatively high degree of wettability, although the individual fibers comprising the cover may not be particularly hydrophilic. The cover material should also contain a great number of relatively large pores. This is because the cover layer is intended to take-up body fluid rapidly and transport it away from the body and the point of deposition. Therefore, the cover layer contributes little to the time taken for the absorbent article to absorb a given quantity of liquid (penetration time).

Advantageously, the fibers which make up the cover layer should not lose their physical properties when they are wetted, in other words they should not collapse or lose their resiliency when subjected to water or body fluid. The cover layer may be treated to allow fluid to pass through it readily. The cover layer also functions to transfer the fluid quickly to the underlying layers of the absorbent article. Thus, the cover layer is advantageously wettable, hydrophilic and porous. When composed of synthetic hydrophobic fibers such as polyester or bi-component fibers, the cover layer may be treated with a surfactant to impart the desired degree of wettability.

Alternatively, the cover layer can also be made of polymer film having large pores. Because of such high porosity, the film accomplishes the function of quickly transferring body fluid to the inner layers of the underlying absorbent layers. A suitable cover material of this type is commercially found on the STAYFREE Dry Max Ultrathin product distributed by McNeil-PPC, Inc.

The cover layer may be attached to the underlying absorbent layers and/or the barrier layer, by adhesion and/or other suitable means know to those of skill in the art.

Absorbent Layer

The absorbent layer may be composed of fibrous materials, such as wood pulp, polyester, rayon, flexible foam, or the like, or combinations thereof. The absorbent layer may also optionally include a superabsorbent polymer (SAP) material. The absorbent layer may also comprise thermoplastic fibers for the purpose of stabilizing the layer and maintaining its structural integrity. The absorbent layer may be treated with surfactant on one or both sides in order to increase its wettability, although generally the absorbent layer is relatively hydrophilic and may not require treatment. The absorbent layer is optionally bonded on both sides to the adjacent layers, i.e. the cover layer and underlying second absorbent layer or barrier layer.

In specific embodiments of the present invention the absorbent layer may be a "transfer" layer. The transfer layer provides means for receiving body fluid from the fluid-pervious cover layer and holding it until a second absorbent layer has an opportunity to absorb it. The transfer layer is, optionally, more dense than the fluid-pervious cover layer and has a larger proportion of smaller pores than does the latter. These attributes allow the transfer layer to contain body fluid and hold it away from the outer side of the fluid-pervious cover layer, thereby preventing the fluid from re-wetting the fluid-pervious cover layer and its surface. However, the transfer layer is optionally not so dense as to prevent the passage of the fluid through the transfer layer and into the underlying second absorbent layer.

When constructed as a transfer layer, the first absorbent layer may comprise various materials, including, for example, cellulose fibers such as from wood pulp, single component or bicomponent fibers that include thermoplastic materials (such as polyester, polypropylene, polyethylene, among others) in fiber or other forms, rayon, organic binders (such as copolymers of vinyl, acrylic and/or other monomers that may be coated onto thermoplastic fibers or otherwise incorporated into the transfer layer) among other materials known to the art.

Second Absorbent Layer

The absorbent article of the present invention may comprise one or more absorbent layers. The second or any additional absorbent layers may comprise a single layer of material or may comprise multiple layers. In certain embodiments of the present invention the second absorbent layer functions as the absorbent core of the absorbent article. Optionally, such absorbent core has a high total absorbent capacity and function to hold fluid upon receiving such fluid from the transfer layer. In addition, the absorbent core optionally has a greater density than that of the transfer layer.

In one embodiment, the second absorbent layer is a blend or mixture of cellulosic fibers and superabsorbent disposed therein. Cellulosic fibers that can be used in the second absorbent layer are well known in the art and include wood pulp, cotton, flax and peat moss. Optionally, wood pulp is used in the second absorbent layer. Pulps can be obtained from mechanical or chemi-mechanical, sulfite, kraft, pulping reject materials, organic solvent pulps, etc. Both softwood and hardwood species are useful. Optionally, softwood pulp is used in the second absorbent layer. It is not necessary to treat cellulosic fibers with chemical debonding agents, cross-linking agents and the like for use in the present material. Some portion of the pulp may be chemically treated as discussed in U.S. Pat. No. 5,916,670 to Tan et al., herein incorporated by reference, to improve flexibility of the product. Flexibility of the material may also be improved by mechanically working the material or tenderizing the material.

The second absorbent layer can contain any superabsorbent polymer (SAP) which are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. In certain embodiments, the superabsorbent polymer particles are crosslinked polyacrylates, such as the product offered by Sumitomo Seika Chemicals Co., Ltd. Of Osaka, Japan, under the designation of SA70N and products offered by Stockhausen Inc. In a specific example, the second absorbent layer is a material containing from 90% to about 40% percent cellulosic fiber, and about 10% to about 60% SAP. The second absorbent layer may comprise a material manufactured by using air-laying means well known in the art.

Barrier Layer

Underlying the first absorbent layer or the second absorbent layer is a barrier layer comprising liquid-impervious film material so as to prevent liquid that is entrapped in the absorbent layer from egressing the absorbent article and staining the wearer's undergarment. The barrier layer is optionally made of polymeric film, although it may be made of liquid impervious, air-permeable material such as repellent-treated non-woven or micropore films or foams.

The barrier layer may be breathable, i.e., permits vapor to transpire. Known materials for this purpose include nonwoven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet.

The cover layer and the barrier layer are optionally joined along their marginal portions so as to form an enclosure or flange seal that maintains the absorbent layers and captive. The joint may be made by means of adhesives, heat-bonding, ultrasonic bonding, radio frequency sealing, mechanical crimping, and the like and combinations thereof.

Positioning adhesive may be applied to a garment facing surface of the barrier layer for securing the absorbent article to a garment during use. The positioning adhesive may be covered with removable release paper so that the positioning adhesive is covered by the removable release paper prior to use.

Absorbent articles of this invention may or may not include wings 200 (or, alternatively, flaps or tabs) for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg; U.S. Pat. No. 4,900,320 to McCoy; and U.S. Pat. No. 4,608,047 to Mattingly. The disclosures of each of these patents are herein incorporated by reference. As disclosed in the above documents, wings 200 are generally speaking flexible and configured to be folded over the edges of the underwear so that the wings 200 are disposed between the edges of the underwear.

Additionally, any of the above described layers, optionally the cover and/or barrier layers may be micro-embossed, have a printed design, have a printed message to the consumer, and/or may be at least partially colored.

The Deformation/Distribution Test

The Deformation and Distribution Test simulates how the absorbent article will deform and, at the same time, function to distribute fluid under realistic wearing conditions. The deformed shape of the absorbent article influences where fluid exiting the body contacts the absorbent article. Once fluid contacts the absorbent article, the absorbent structure (and any embossing contained on the body facing surface thereof) will affect how it is distributed from contact onward. Ideally, fluid is concentrated along the longitudinal center line of the absorbent article and as more fluid contacts the article, the fluid spreads primarily along the length of the absorbent article, maintaining a distance from the edges of the absorbent article. Absorbent articles resulting in this type of fluid contact and distribution give the consumer confidence that leakage will not occur.

Figure 6:
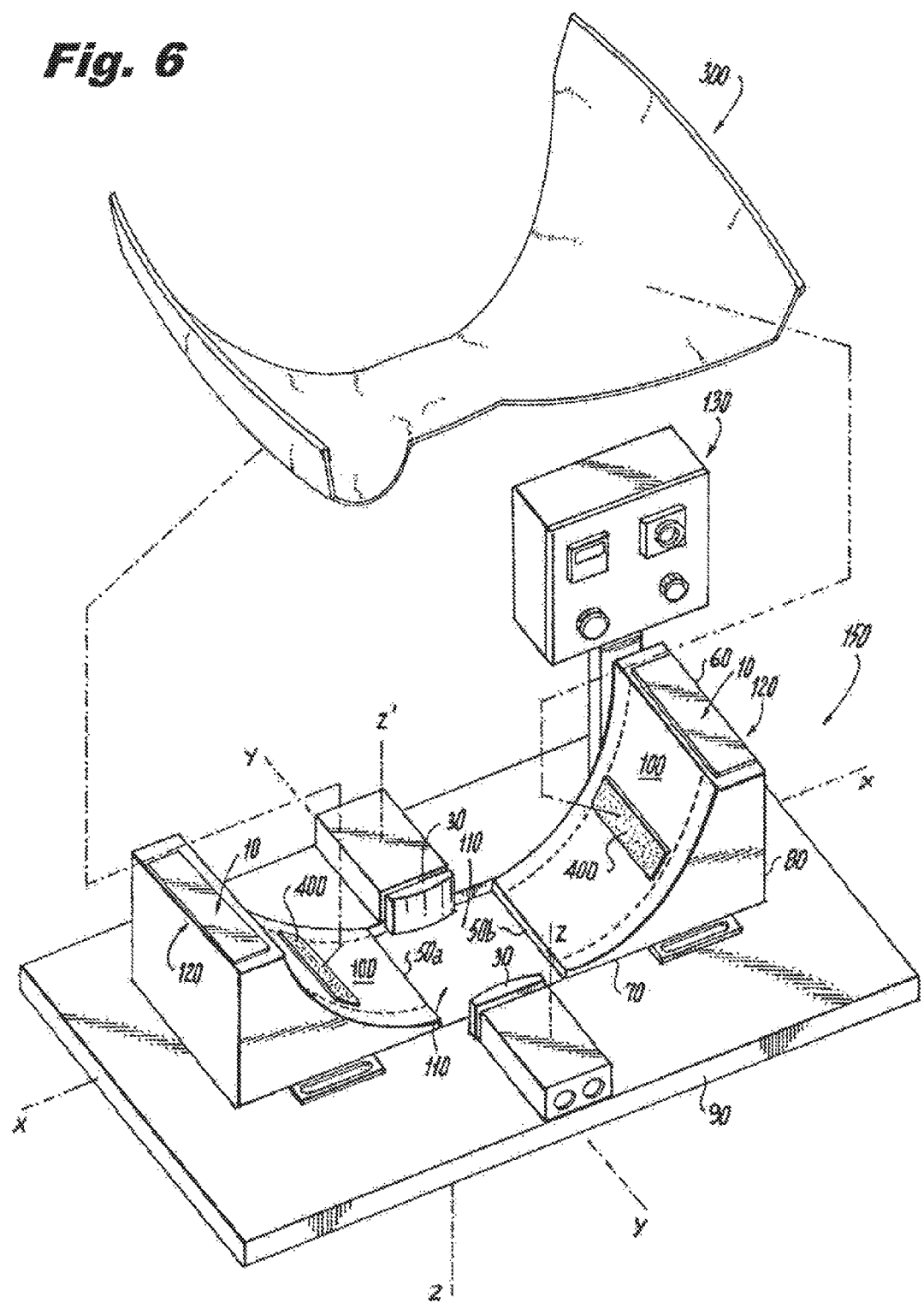
FIG. 6 is a perspective view of the deformation and fluid distribution testing device 150 and panty 300 for placement onto device 150 prior to testing.
Figure 7:
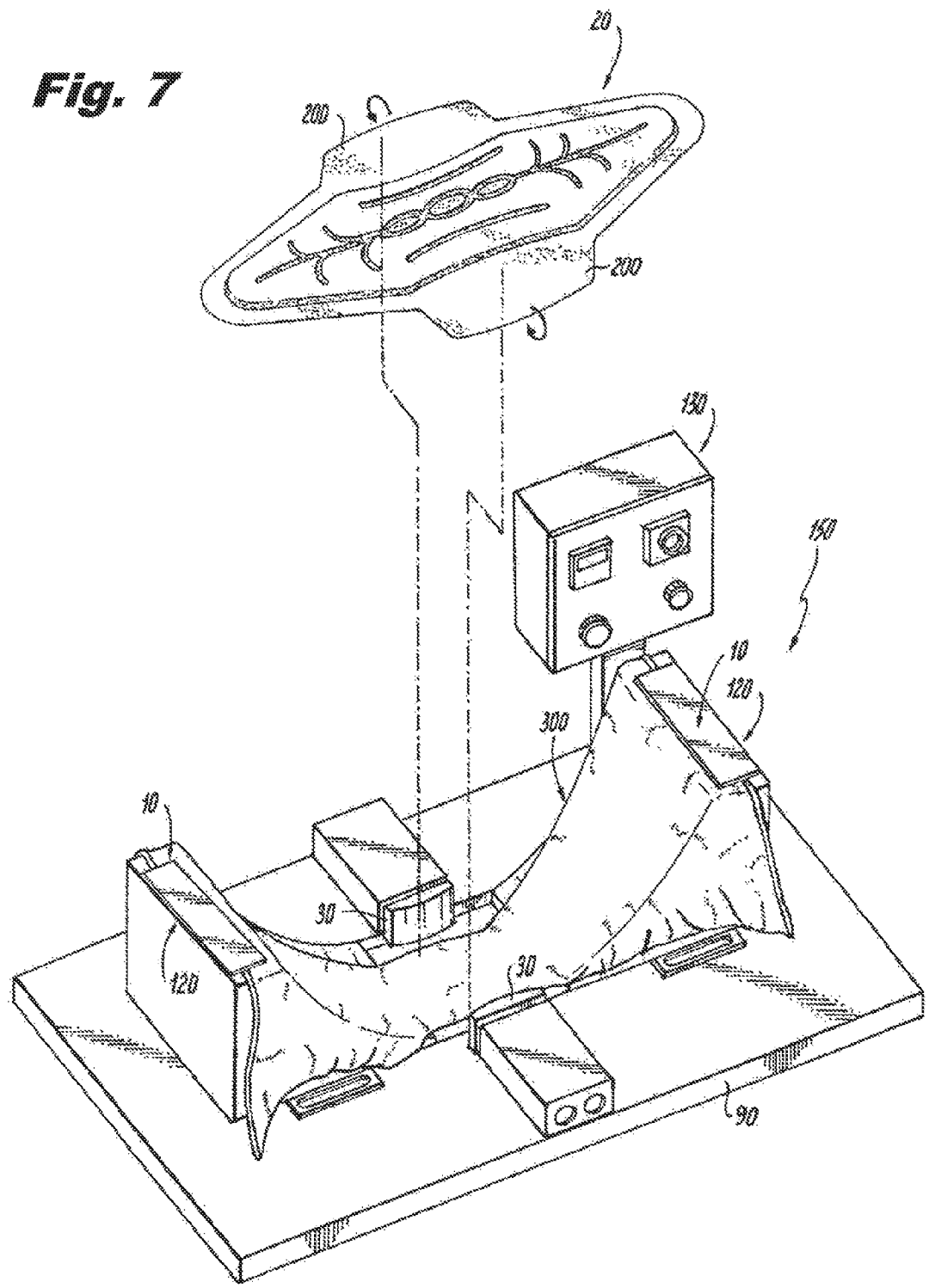
FIG. 7 is a perspective view of the deformation and fluid distribution testing device, showing placement of the panty 300 and positioning of article 20 for placement in preparation for testing.
Figure 8:
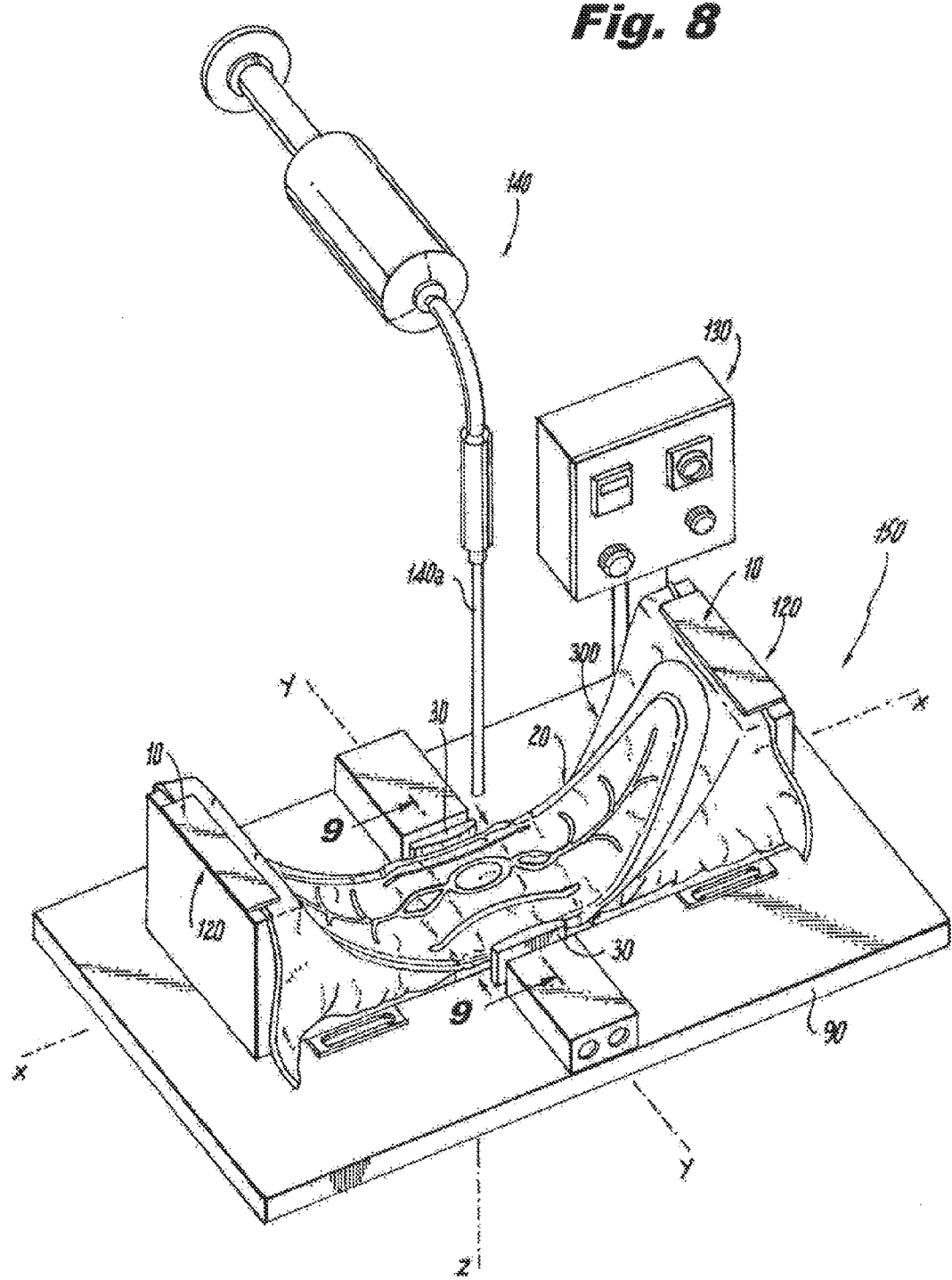
FIG. 8 is a perspective view of the deformation and fluid distribution testing device 150 in operation.
Figure 9:
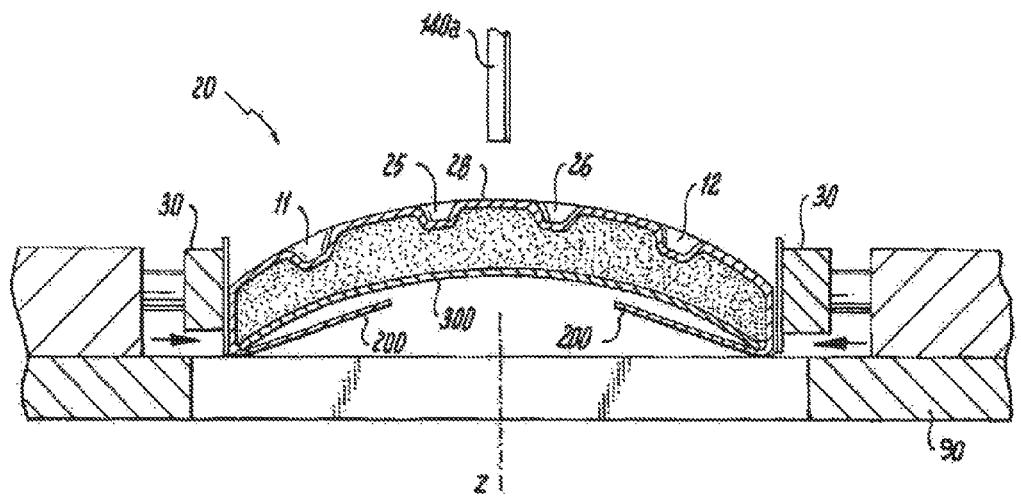
FIG. 9 is a cross-sectional view of the deformation and fluid distribution testing device 150 in operation taken along line 9-9 in FIG. 8, showing hump deformation as movement away from x, y plane of FIG. 8 upward in the direction of the z axis.
Figure 10:
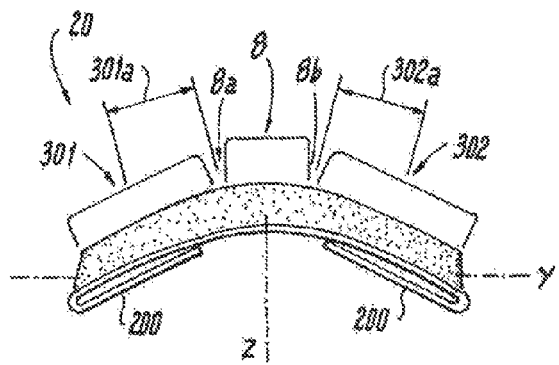
FIG. 10 is a cross sectional view of an absorbent article forming a type of a hump deformation along the longitudinal centerline.
Figure 11:
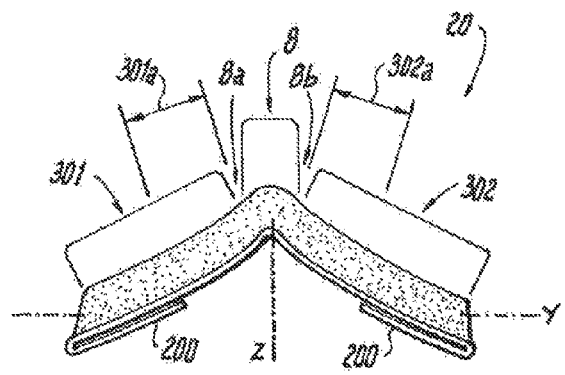
FIG. 11 is a cross sectional view of an absorbent article forming a type of a hump deformation along the longitudinal centerline.
Figure 12:
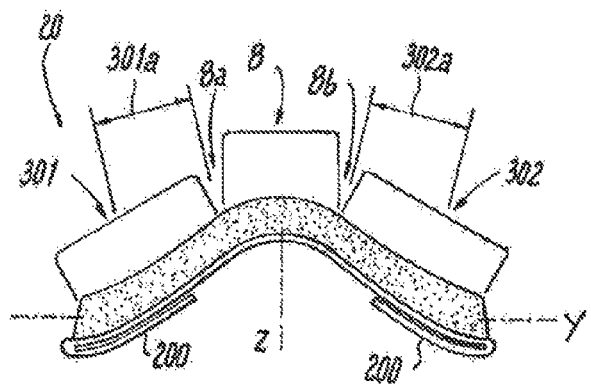
FIG. 12 is a cross sectional view of an absorbent article forming a type of a hump deformation along the longitudinal centerline.
Figure 13:
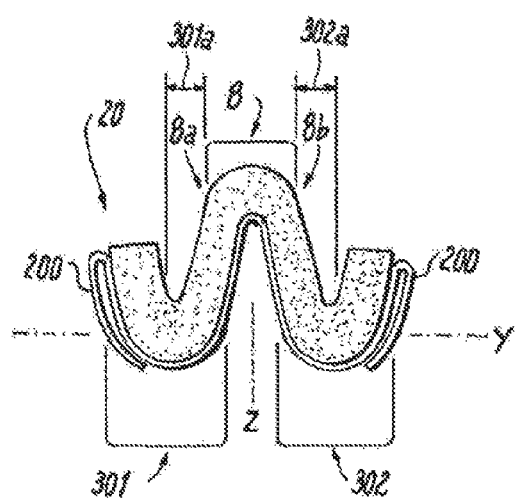
FIG. 13 is a cross sectional view of an absorbent article forming a type of a hump deformation along the longitudinal centerline.
Figure 14:
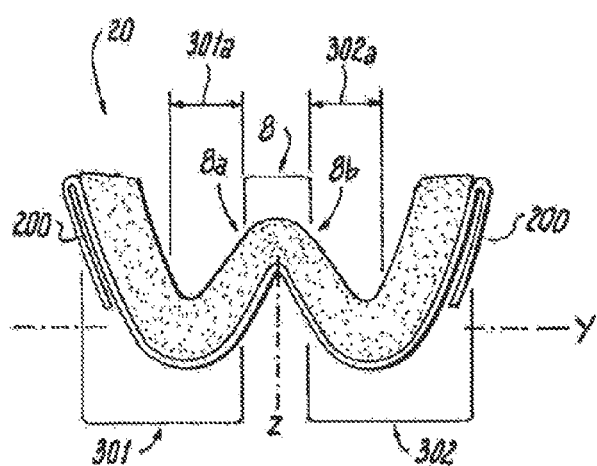
FIG. 14 is a cross sectional view of an absorbent article forming a type of a hump deformation along the longitudinal centerline.
Figure 15:
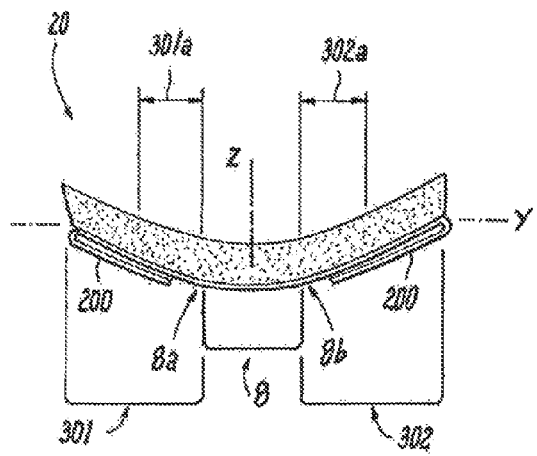
FIG. 15 is a cross sectional view of an absorbent article forming a type of a cup deformation along the longitudinal centerline.
Figure 16:
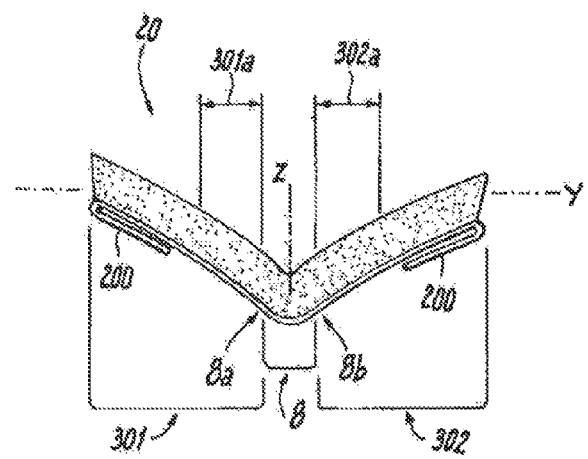
FIG. 16 is a cross sectional view of an absorbent article forming a type of a cup deformation along the longitudinal centerline.
Figure 17:
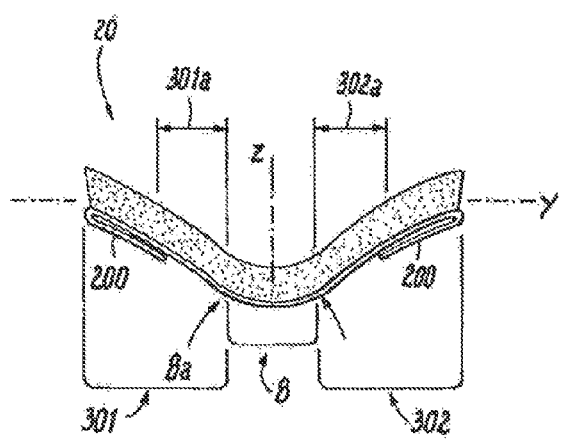
FIG. 17 is a cross sectional view of an absorbent article forming a type of a cup deformation along the longitudinal centerline.
Figure 18:
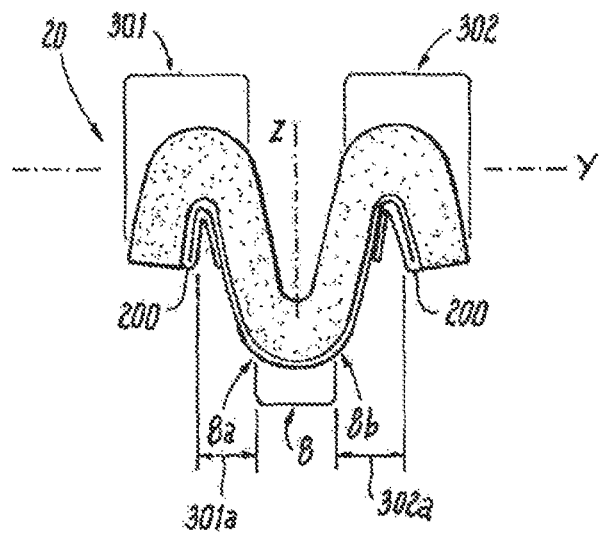
FIG. 18 is a cross sectional view of an absorbent article forming a type of a cup deformation along the longitudinal centerline.
Figure 19:
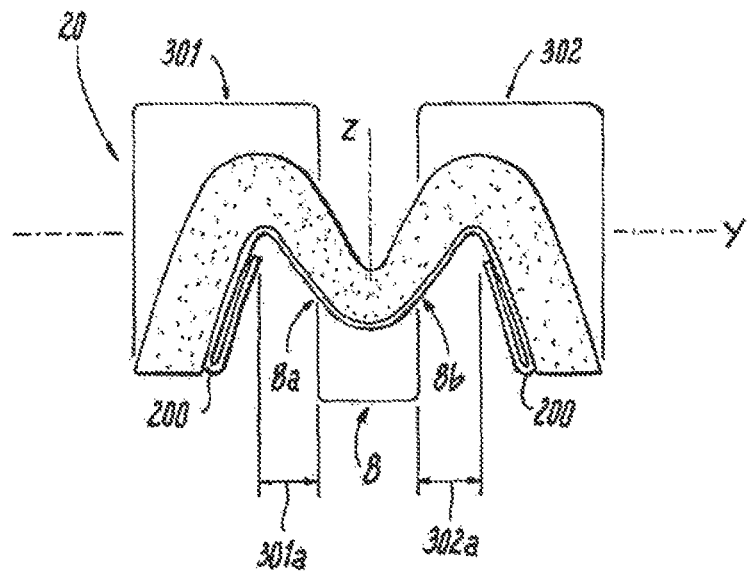
FIG. 19 is a cross sectional view of an absorbent article forming a type of a cup deformation along the longitudinal centerline.
Figure 20:
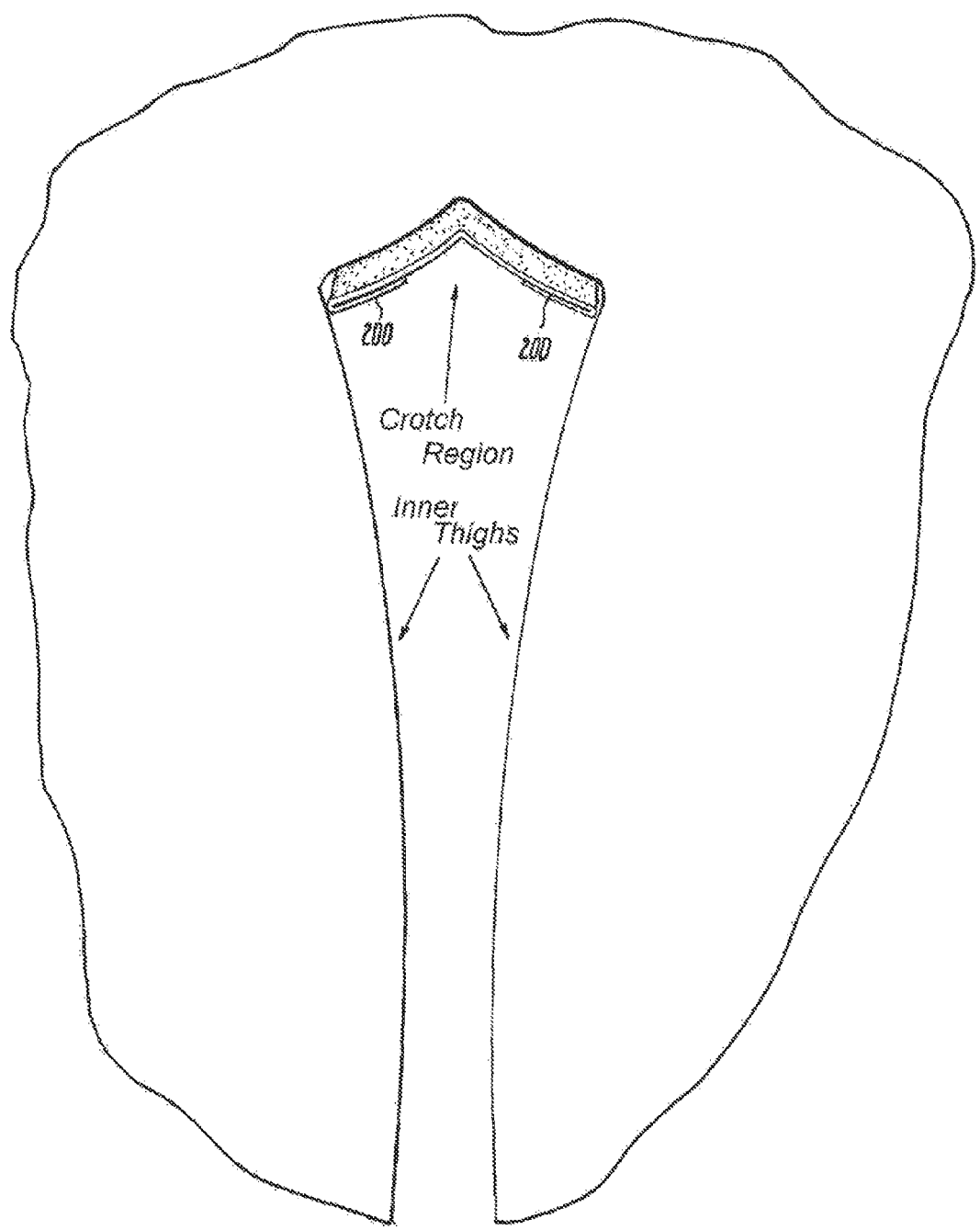
FIG. 20 is a cross sectional view of an absorbent article forming a hump deformation for positioning the absorbent article closer to a user during use.

The device 150 used in performing the Deformation/Distribution Test is depicted in FIGS. 6 to 8 and is a modified version the device described in U.S. Pat. No. 5,607,414 to Richards et al., which patent is herein incorporated by reference. The support blocks 10 have curved surfaces as shown in FIG. 6 with a radius of curvature equal to 92 mm. The longitudinal distance (along x axis) between points 50a and 50b of the support blocks 10, shown in FIG. 6 is 77 mm. At points 50a and 50b, the tangent to the curved surfaces is parallel to the horizontal plane. The edge 60 of support blocks 10 has a width of 80 mm. The edge 70 of support blocks 10 has a length of 105 mm. The edge 80 of support blocks 10 has a height of 75 mm. The compression plates 30 have a length of 70 mm measured along the compression plates 30 in the direction from point 50a to point 50b (along x axis parallel to edge 70) and have a radius of 224 mm measured with respect to the vertical axis z' of FIG. 6. The compression plates have a width of 34 mm in the direction of the vertical axis z.

The support blocks 10 are fixedly secured on a base plate 90 having a thickness of 12 mm. Points 50a and 50b are about 5 mm above the upper surface of the base plate 90. The bottom surfaces of the compression plates 30 are coplanar with the upper surface of the base plate 90. The base plate has a 90 mm long by 77 mm wide through cut out area 110 extending between the two support blocks.

A panty 300 as described below is cut at each hip section so that it can be laid flat as shown in FIG. 7. Strips of double stick tape 400 are placed on the two test support blocks 10 in regions 100 (region 100 is depicted as the region between the dashed lines on the curved surfaces of blocks 10 in FIG. 6). The adhesive type 400 is Tectape, code 633, supplied by Day Brasil. The adhesive tape regions 100 are each 65 mm wide in the direction of edge 60 and cover the entire curved surface of the support blocks in the direction perpendicular to edge 60. The cut garment is then laid onto the two supports such that the crotch bridges the region between the support blocks 10 as shown in FIG. 7. The panty 300 is placed so that there is no significant tension in the fabric but it also has no slack. The panty is also placed so that there is no wrinkling or stretching of the garment in the adhesive tape regions 100. Also, the narrowest section of the crotch section is centered between the support blocks 10. In addition each support block has a clamp 120 to aid in holding down the garment.

A test article sample is prepared by removing an absorbent article product from its packaging and removing any other release papers from the product. The article sample is placed on the support blocks 10 so that the entire area of the article sample's central positioning adhesive sticks to the panty 300. Wings 200 of the article sample (if any) are wrapped around and stuck to the backside of the panty (i.e., the side of the panty facing the device). It is critical to avoid deforming the central region 3 of the absorbent core of the article sample while placing it on the support and wrapping and sticking the wings 200 to the backside side of the panty. Wrapping of the wings 200 around the panty is performed so that the each wing is wrapped as far as possible on the backside of the panty 300 such that the panty is not gathered or deformed. Finger pressure is applied to insure the wing 200 is adhered to the backside of the panty 300.

The compression plates 30 of the device 150 are positioned at a starting distance (or first position) of 65 mm from each other. The compression plates 30 are compressed (or moved) together at a speed of 15 mm/sec until they are separated from each other by 25 mm (or second position), the compression plates 30 are, then, moved apart at a speed of 15 mm/sec until they are again separated from each other by 65 mm (first position). The specified distances 25 and 65 mm are based on the nearest points on the compression plates facing article sample 20 and panty 300 once the article and panty are positioned on the device for testing. In a specific embodiment, compression (or movement) of compression plates 30 is accomplished by pneumatic cylinders; however, other compression driving mechanisms capable of providing the above compression and return movements may optionally be used such as servo motors. A control box (130) may be mounted on the apparatus for actuating test and controlling test parameters (e.g., number of test cycles and test cycle speeds).

After three compressions, the article sample is held in the compressed (or deformed) state (i.e., not returned to its starting position) and the deformation is visually inspected to determine formation of either a "hump", "cup" or "bunch" configuration.

The above described procedure is repeated 10 times on separate test article samples. The occurrence of "hump", "cup" or "bunch" is recorded at the end of each test procedure. The percentage of procedures resulting in a "hump" deformation occurrence is calculated. The articles of the present invention deform into a hump deformation in at least about 75%, optionally, at least about 80%, optionally, at least about 85%, optionally at least about 90%, optionally, at least about 95% of such repeated procedures.

For each test article, once the test article is deformed as by the above procedure, the article sample is held in the compressed (or deformed) state and the ability of the article sample to wick and distribute fluid along the longitudinal centerline os article sample is assessed as follows:

Synthetic menstrual fluid is prepared by the method disclosed in U.S. Pub. No. 20070219520 to Rosenfeld et al., which publication is herein incorporated by reference. In accordance with this disclosure, test fluid was made of the following mixture to simulate bodily fluids: 49.5% of 0.9% sodium chloride solution (VWR catalog # VW 3257-7), 49.05% Glycerin (Emery 917), 1% Phenoxyethanol (Clariant Corporation Phenoxetol®) and 0.45% Sodium Chloride (Baker sodium chloride crystal #9624-05). Seven ml of test fluid (7 ml) is dropped from distance of 1 mm above the product surface onto the center of the product in its deformed state at a rate of 1 ml/min by means of a commercially available pump 140, ref. PUMP 11 ELITE, supplied by Harvard Apparatus (Plymouth meeting, Pa.) using pipette 140*a* with an inner lumen diameter of 1.5 mm is held vertically over the center of the product with its exit point (i.e., tip equaling 1.5 mm diameter) to drop the referenced synthetic menstrual fluid as described. Once the flow from the pipette has completed, an additional 5 minutes is allowed to lapse and, then, the longest length and widest width of the stain on the product are measured.

The panty used for this test is constructed from woven cotton fabric with elastic leg bands supplied by Marisa in Brazil (supplier code 29771). This type fabric and construction is available in panties in most regions. The crotch of the panty at its narrowest point has a width of between 60 and 70 mm. Certain panties have a section with double layer fabric in the center. At a distance of 50 mm forward and rear of the narrowest point, the panty will have a width between 70 and 80 mm.

From the foregoing description, one skilled in the art can ascertain the essential characteristics of this invention, and without departing from the spirit and scope thereof, can make various changes and modifications. Embodiments set forth by way of illustration or example are not intended as limitations on the variations possible in practicing the present invention.

EXAMPLES

Example I

Frequency of hump deformation and average stain length to stain width ratio of an absorbent article of the present invention as measured by the Deformation/Distribution Test method described above.

Tenabsorbent article samples were prepared using a 15 gsm polypropylene spunbond nonwoven (Spunbond 15) supplied by Polystar, Brazil as the cover layer; 415 gsm cellulose fluff pulp (Grade 4881) supplied by Georgia Pacific, USA as the absorbent layer; and 21 gsm polyethylene film (PE 21) supplied by Clopay, Brazil as the barrier layer. The embossing patterns of FIG. 3 was applied to the regions of absorbent articles as described above with an embossing thickness ranging from 2 mm to 3 mm, when measured from a top surface of the absorbent article at the embossing. The absorbent article samples were tested for hump deformation and longitudinal fluid wicking using the Deformation/Distribution Test method described above. Intimus Gel Noturno pads (Kimberly Clark, Brazil—Comparative 1) and Sempre Livre Tri-Protect pads (Johnson &

Johnson do Brasil, Brazil—Comparative 2) were used as comparative examples. The results are shown in Table 1 below.

TABLE 1

| Sample | # samples tested | % frequency of hump deformation | Average length over width stain size ratio |
|---|---|---|---|
| Example 1 | 20 | 100 | 2.5 |
| Comparative 1 | 20 | 0 | 2.3 |
| Comparative 2 | 20 | 0 | 2.6 |

As illustrated by the above description and the accompanying drawings absorbent articles according to the present invention provide a structure that enables such article to provide superior wicking characteristics and controlled deformation.

We claim:

1. An absorbent article having a transversely extending centerline and a longitudinally extending centerline and a body facing surface, the body facing surface comprising:
    a central region having i) a first transverse side parallel to the transversely extending centerline and a second transverse side parallel to the transversely extending centerline and opposite the first transverse side in the direction of the longitudinally extending centerline; and ii) a first longitudinal side parallel to the longitudinally extending centerline and a second longitudinal side parallel to the longitudinally extending centerline and opposite the first longitudinal side in the direction of the transversely extending centerline, the central region comprising an embossing pattern extending about and directionally along the longitudinally extending centerline, the embossing pattern comprising channels;
    a first longitudinal end region having a length measured from the first transverse side of the central region to a first transverse edge of the absorbent article directionally along the longitudinally extending centerline away from the central region, the first longitudinal end region comprising a first plurality of channels defining a first longitudinal end embossing pattern having a length wherein at least one of the channels of the first plurality of channels extends substantially parallel to the longitudinally extending centerline proximate the longitudinally extending centerline from the first transverse side from about 50% to about 90% of the length of the first longitudinal end region;
    a second longitudinal end region having a length measured from the second transverse side of the central region to a second transverse edge of the absorbent article directionally along the longitudinally extending centerline and away from the of the central region, the second longitudinal end region comprising a second plurality of channels defining a second longitudinal end embossing pattern having a length wherein at least one of the channels of the second plurality of channels extends substantially parallel to the longitudinally extending centerline proximate the longitudinally extending centerline from the second transverse side from about 50% to about 90% of the length of the second longitudinal end region, the embossing pattern of the central region located longitudinally between and interconnected with the first and second plurality of channels;
    a central longitudinal zone extending longitudinally across the first and second transverse end regions and the central region, the central longitudinal zone extending symmetrical about and directionally along the longitudinally extending centerline and comprising opposing longitudinally extending central longitudinal zone edges parallel to the longitudinally extending centerline defining a central longitudinal zone width W of from about 5 mm to about 20 mm, wherein the embossing pattern of the central region is located within the central longitudinal zone and does not extend beyond the central longitudinal zone width W;
    a first transverse end region extending from the first longitudinal side of the central region directionally along the transversely extending centerline and away from the central region, the first transverse end region comprising a least one first longitudinally extending outer channel spaced from about 5 mm to about 26 mm from the nearest central longitudinal zone edge; and
    a second transverse end region extending from the second longitudinal side of the central region directionally along the transversely extending centerline and away from the of the central region, the second transverse end region comprising a least one second longitudinally extending outer channel spaced from about 5 mm to about 26 mm from the nearest central longitudinal zone edge
    wherein the channels of the embossing pattern of the central region interconnects in fluid communication with the channels of the embossing patterns of the first and second longitudinal end regions, thereby defining the first and second transverse sides of the central region.

2. The absorbent article of claim 1, wherein the at least one channel of the first plurality of channels extends directionally along or about a longitudinally extending centerline across from about 65% to about 90% of the first longitudinal end region.

3. The absorbent article of claim 1, wherein the at least one channel of the second plurality of channels extends directionally along or about a longitudinally extending centerline across from about 65% to about 90% of the second longitudinal end region.

4. The absorbent article of claim 1, wherein the at least one channel of the first plurality of channels extends directionally along the longitudinally extending centerline across from about 65% to about 90% of the first longitudinal end region and the at least one channel of the second plurality of channels extends directionally along the longitudinally extending centerline across from about 65% to about 90% of the second longitudinal end region.

5. The absorbent article of claim 1, wherein the at least one channel of the first and second plurality of channels, respectively, comprises at least one first branch(es) and/or at least one second branch(es), respectively.

6. The absorbent article of claim 5, wherein the at least one channel extending directionally along the longitudinally extending centerline of the first and second plurality of channels, respectively, is located within the central longitudinal zone and does not extend beyond the central longitudinal zone width W.

7. The absorbent article of claim 5, wherein at least one first branch(es) and/or second branch(es), respectively, is located within the central longitudinal zone and extends beyond the central longitudinal zone width W.

8. The absorbent article of claim 6, wherein the first branch(es) and/or second branch(es), respectively, of the at least one channel extending directionally along the longitudinally extending centerline of the first and second plurality of channels, respectively, is located within the central longitudinal zone and extends beyond the central longitudinal zone width W.

9. The absorbent article of claim 1, wherein the central longitudinal zone width W is from about 10 mm to about 18 mm.

10. The absorbent article of claim 1, wherein the first longitudinally extending outer channel is spaced from about 10 mm to about 20 mm from the nearest central longitudinal zone edge.

11. The absorbent article of claim 1, wherein the second longitudinally extending outer channel is spaced from about 10 mm to about 20 mm from the nearest central longitudinal zone edge.

12. The absorbent article of claim 1, wherein one or each of the first and second longitudinally extending outer channels extends and connects with the other longitudinally extending outer channel to unite their respective ends such that the outer embossing pattern surrounds or substantially surrounds the central embossing pattern and the first and second plurality of channels.

13. An absorbent article having a transversely extending centerline and a longitudinally extending centerline and a body facing surface, the body facing surface comprising:
  a central region having i) a first transverse side parallel to the transversely extending centerline and a second transverse side parallel to the transversely extending centerline and opposite the first transverse side in the direction of the longitudinally extending centerline; and ii) a first longitudinal side parallel to the longitudinally extending centerline and a second longitudinal side parallel to the longitudinally extending centerline and opposite the first longitudinal side in the direction of the transversely extending centerline, the central region comprising an embossing pattern extending about and directionally along the longitudinally extending centerline, the embossing pattern comprising channels;
  a first longitudinal end region having a length measured from the first transverse side of the central region to a first transverse edge of the absorbent article directionally along the longitudinally extending centerline away from the central region, the first longitudinal end region comprising a first plurality of channels defining a first longitudinal end embossing pattern having a length wherein at least one of the channels of the first plurality of channels extends substantially parallel to the longitudinally extending centerline proximate the longitudinally extending centerline from the first transverse side from about 50% to about 90% of the length of the first longitudinal end region;
  a second longitudinal end region having a length measured from the second transverse side of the central region to a second transverse edge of the absorbent article directionally along the longitudinally extending centerline and away from the of the central region, the second longitudinal end region comprising a second plurality of channels defining a second longitudinal end embossing pattern having a length wherein at least one of the channels of the second plurality of channels extends substantially parallel to the longitudinally extending centerline proximate the longitudinally extending centerline from the second transverse side from about 50% to about 90% of the length of the second longitudinal end region, the embossing pattern of the central region located longitudinally between and interconnected with the first and second plurality of channels;
  a central longitudinal zone extending longitudinally across the first and second transverse end regions and the central region, the central longitudinal zone extending symmetrical about and directionally along the longitudinally extending centerline and comprising opposing longitudinally extending central longitudinal zone edges parallel to the longitudinally extending centerline defining a central longitudinal zone width W of from about 5 mm to about 20 mm, wherein the embossing pattern of the central region is located within the central longitudinal zone and does not extend beyond the central longitudinal zone width W;
  a first transverse end region extending from the first longitudinal side of the central region directionally along the transversely extending centerline and away from the central region, the first transverse end region comprising a least one first longitudinally extending outer channel spaced from about 5 mm to about 26 mm from the nearest central longitudinal zone edge; and
  a second transverse end region extending from the second longitudinal side of the central region directionally along the transversely extending centerline and away from the of the central region, the second transverse end region comprising a least one second longitudinally extending outer channel spaced from about 5 mm to about 26 mm from the nearest central longitudinal zone edge
  wherein the channels of the embossing pattern of the central region interconnects in fluid communication with the channels of the embossing patterns of the first and second longitudinal end regions, thereby defining the first and second transverse sides of the central region;
  and wherein the embossing pattern of the central region, the embossing patterns of the first and second transverse end regions and the embossing patterns of the first and second longitudinal end regions cooperate to facilitate deformation of the article into a hump shaped deformation upon application of the article to a user's crotch region where the body facing surface is aligned to contact a user's body.

* * * * *